United States Patent
Green et al.

(10) Patent No.: US 10,575,504 B2
(45) Date of Patent: *Mar. 3, 2020

(54) NON-HUMAN MAMMALS FOR THE PRODUCTION OF CHIMERIC ANTIBODIES

(71) Applicant: ABLEXIS, LLC, San Diego, CA (US)

(72) Inventors: Larry Green, San Francisco, CA (US); Hiroaki Shizuya, South Pasadena, CA (US)

(73) Assignee: ABLEXIS, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/095,917

(22) Filed: Apr. 11, 2016

(65) Prior Publication Data

US 2016/0219850 A1 Aug. 4, 2016

Related U.S. Application Data

(62) Division of application No. 13/121,883, filed as application No. PCT/US2009/059131 on Sep. 30, 2009, now Pat. No. 9,346,873.

(60) Provisional application No. 61/101,938, filed on Oct. 1, 2008, provisional application No. 61/101,597, filed on Sep. 30, 2008.

(51) Int. Cl.
| | |
|---|---|
| *C07H 21/02* | (2006.01) |
| *C12N 15/63* | (2006.01) |
| *A01K 67/00* | (2006.01) |
| *A01K 67/027* | (2006.01) |
| *C12N 15/85* | (2006.01) |
| *C07K 16/00* | (2006.01) |
| *C07K 16/28* | (2006.01) |
| *C07K 16/46* | (2006.01) |

(52) U.S. Cl.
CPC .......... *A01K 67/0278* (2013.01); *C07K 16/00* (2013.01); *C07K 16/283* (2013.01); *C07K 16/462* (2013.01); *C12N 15/8509* (2013.01); *A01K 2207/15* (2013.01); *A01K 2217/052* (2013.01); *A01K 2217/072* (2013.01); *A01K 2217/15* (2013.01); *A01K 2227/105* (2013.01); *A01K 2267/01* (2013.01); *C07K 2317/14* (2013.01); *C07K 2317/21* (2013.01); *C07K 2317/24* (2013.01); *C07K 2317/51* (2013.01); *C07K 2317/515* (2013.01); *C07K 2317/52* (2013.01); *C07K 2317/522* (2013.01); *C07K 2317/524* (2013.01); *C07K 2317/526* (2013.01); *C07K 2317/53* (2013.01); *C07K 2317/56* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,204,244 A | 4/1993 | Fell |
| 5,464,764 A | 11/1995 | Capecchi et al. |
| 5,487,992 A | 1/1996 | Capecchi et al. |
| 5,545,806 A | 8/1996 | Lonberg et al. |
| 5,545,807 A | 8/1996 | Surani et al. |
| 5,569,825 A | 10/1996 | Lonberg et al. |
| 5,591,669 A | 1/1997 | Krimpenfort |
| 5,612,205 A | 3/1997 | Kay et al. |
| 5,625,126 A | 4/1997 | Lonberg et al. |
| 5,627,059 A | 5/1997 | Capecchi et al. |
| 5,631,153 A | 5/1997 | Capecchi et al. |
| 5,633,425 A | 5/1997 | Lonberg et al. |
| 5,654,182 A | 8/1997 | Wahl et al. |
| 5,661,016 A | 8/1997 | Lonberg et al. |
| 5,677,177 A | 10/1997 | Wahl et al. |
| 5,721,367 A | 2/1998 | Kay et al. |
| 5,770,429 A | 6/1998 | Lonberg et al. |
| 5,789,215 A | 8/1998 | Berns et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,885,836 A | 3/1999 | Wahl et al. |
| 5,939,598 A | 8/1999 | Kucherlapati et al. |
| 6,023,010 A | 2/2000 | Krimpenfort et al. |
| 6,075,181 A | 6/2000 | Kucherlapati et al. |
| 6,090,554 A | 7/2000 | Woychik et al. |
| 6,091,001 A | 7/2000 | Jakobovits et al. |

(Continued)

FOREIGN PATENT DOCUMENTS

| | | |
|---|---|---|
| EP | 1 399 559 B1 | 4/2008 |
| WO | WO 1990/00616 | 1/1990 |

(Continued)

OTHER PUBLICATIONS

Bankovich et al., Structural Insight into Pre-B Cell Receptor Function Science Apr. 13, 2007: vol. 316, Issue 5822, pp. 291-294.*
Hirabayashi Kinetic analysis of the interactions of recombinant human VpreB and Ig V domains J Immunol 1995; 155:1218-1228.*
Hybridoma technology—Wikipedia Hybridoma technology From Wikipedia, the free encyclopedia pp. 1-4 ; dowloaded Jun. 26, 2017.*
Jefferis et al 2009, Recombinant antibody therapeutics:the impact of glycosylation on mechanisms of action Trends in Pharmacological Sciences vol. 30 No. 7 pp. 356-362.*

(Continued)

*Primary Examiner* — Maria G Leavitt
(74) *Attorney, Agent, or Firm* — Haley Guiliano LLP; James F. Haley, Jr.; Brian M. Gummow

(57) ABSTRACT

The invention provides knock-in non-human cells and mammals having a genome encoding chimeric antibodies and methods of producing knock-in cells and mammals. Certain aspects of the invention include chimeric antibodies, humanized antibodies, pharmaceutical compositions and kits. Certain aspects of the invention also relate to diagnostic and treatment methods using the antibodies of the invention.

13 Claims, 15 Drawing Sheets

(56) References Cited

U.S. PATENT DOCUMENTS

| | | |
|---|---|---|
| 6,114,598 A | 9/2000 | Kucherlapati et al. |
| 6,130,364 A | 10/2000 | Jakobovits et al. |
| 6,150,584 A | 11/2000 | Kucherlapati et al. |
| 6,162,963 A | 12/2000 | Kucherlapati et al. |
| 6,204,061 B1 | 3/2001 | Capecchi et al. |
| 6,348,349 B1 | 2/2002 | Bruggemann |
| 6,528,313 B1 | 3/2003 | Le Mouellic et al. |
| 6,528,314 B1 | 3/2003 | Le Mouellic et al. |
| 6,570,061 B1 | 5/2003 | Rajewsky et al. |
| 6,586,251 B2 | 7/2003 | Economides et al. |
| 6,596,541 B2 | 7/2003 | Murphy et al. |
| 6,632,976 B1 | 10/2003 | Tomizuka et al. |
| 6,638,768 B1 | 10/2003 | Le Mouellic et al. |
| 6,653,113 B1 | 11/2003 | Berns et al. |
| 6,657,103 B1 | 12/2003 | Kucherlapati et al. |
| 6,673,986 B1 | 1/2004 | Kucherlapati et al. |
| 6,689,610 B1 | 2/2004 | Capecchi et al. |
| 6,774,279 B2 | 8/2004 | Dymecki |
| 6,794,132 B2 | 9/2004 | Buechler et al. |
| 6,833,268 B1 | 12/2004 | Green et al. |
| 6,852,530 B2 | 2/2005 | Silver et al. |
| 6,956,146 B2 | 10/2005 | Wahl et al. |
| 6,998,514 B2 | 2/2006 | Bruggemann |
| 7,041,870 B2 | 5/2006 | Tomizuka et al. |
| 7,041,871 B1 | 5/2006 | Lonberg et al. |
| 7,049,426 B2 | 5/2006 | Green et al. |
| 7,064,244 B2 | 6/2006 | Jakobovits et al. |
| 7,105,348 B2 | 9/2006 | Murphy et al. |
| 7,145,056 B2 | 12/2006 | Jakobovits et al. |
| 7,205,148 B2 | 4/2007 | Economides et al. |
| 7,235,360 B2 | 6/2007 | Reff et al. |
| 7,371,577 B2 | 5/2008 | Wahl et al. |
| 7,435,871 B2 | 10/2008 | Green |
| 7,501,552 B2 | 3/2009 | Lonberg et al. |
| 7,541,513 B2 | 6/2009 | Bruggeman et al. |
| 7,547,817 B2 | 6/2009 | Green et al. |
| 7,722,871 B2 | 5/2010 | Casterman et al. |
| 7,910,798 B2 | 3/2011 | Tanamachi et al. |
| 8,629,317 B2 | 1/2014 | Cogne et al. |
| 8,754,287 B2 | 6/2014 | MacDonald et al. |
| 9,346,873 B2 | 5/2016 | Green et al. |
| 9,365,655 B2 * | 6/2016 | Craig ............... C07K 16/00 |
| 9,445,581 B2 | 9/2016 | Bradley |
| 9,580,491 B2 | 2/2017 | Green et al. |
| 2003/0135872 A1 | 7/2003 | Burgess, Jr. et al. |
| 2003/0222218 A1 | 12/2003 | Nozu |
| 2003/0229905 A1 | 12/2003 | Kucherlapati et al. |
| 2004/0025031 A1 | 2/2004 | Ooi et al. |
| 2004/0107452 A1 | 6/2004 | Berns et al. |
| 2004/0128703 A1 | 7/2004 | Shizuya |
| 2004/0203153 A1 | 10/2004 | Le Mouellic et al. |
| 2004/0214222 A1 | 10/2004 | Burgess, Jr. et al. |
| 2004/0231012 A1 | 11/2004 | Bruggemann |
| 2005/0038232 A1 | 2/2005 | Karrer et al. |
| 2005/0118648 A1 | 6/2005 | Li |
| 2005/0149998 A1 | 7/2005 | Capecchi et al. |
| 2005/0238645 A1 | 10/2005 | Gold et al. |
| 2005/0261480 A1 | 11/2005 | Foote |
| 2006/0015949 A1 | 1/2006 | Lonberg et al. |
| 2006/0015957 A1 | 1/2006 | Londberg |
| 2006/0040363 A1 | 2/2006 | Kucherlapati et al. |
| 2006/0117398 A1 | 6/2006 | Buelow et al. |
| 2006/0134780 A1 | 6/2006 | Green et al. |
| 2007/0009957 A1 | 1/2007 | Bowdish et al. |
| 2007/0061900 A1 | 3/2007 | Murphy et al. |
| 2007/0092505 A1 | 4/2007 | Buelow et al. |
| 2007/0209083 A1 * | 9/2007 | Thiam ............... C07K 14/70517 800/14 |
| 2008/0098490 A1 | 4/2008 | Jakobovits et al. |
| 2008/0182331 A1 | 7/2008 | Le Mouellic et al. |
| 2009/0098134 A1 | 4/2009 | Buelow |
| 2009/0260093 A1 | 10/2009 | Tanamachi |
| 2010/0077497 A1 | 3/2010 | Deshpande |
| 2010/0287629 A1 | 11/2010 | Lonberg et al. |
| 2011/0236378 A1 | 9/2011 | Green et al. |
| 2012/0070861 A1 | 3/2012 | Macdonald et al. |
| 2013/0167256 A1 | 6/2013 | Green et al. |
| 2016/0219848 A1 | 8/2016 | Green et al. |
| 2016/0219849 A1 | 8/2016 | Green et al. |
| 2016/0222090 A1 | 8/2016 | Green et al. |
| 2016/0222091 A1 | 8/2016 | Green et al. |
| 2016/0222092 A1 | 8/2016 | Green et al. |
| 2016/0222093 A1 | 8/2016 | Green et al. |
| 2017/0181414 A1 | 6/2017 | Green et al. |
| 2017/0188557 A1 | 7/2017 | Green et al. |
| 2017/0188558 A1 | 7/2017 | Green et al. |
| 2017/0190794 A1 | 7/2017 | Green et al. |
| 2017/0190795 A1 | 7/2017 | Green et al. |
| 2017/0190796 A1 | 7/2017 | Green et al. |
| 2017/0190797 A1 | 7/2017 | Green et al. |
| 2017/0218090 A1 | 8/2017 | Green et al. |

FOREIGN PATENT DOCUMENTS

| | | | |
|---|---|---|---|
| WO | WO 1990/04036 A1 | | 4/1990 |
| WO | WO 1990/11354 A1 | | 10/1990 |
| WO | WO 1991/00906 A1 | | 1/1991 |
| WO | WO 1991/10741 A1 | | 7/1991 |
| WO | WO 1991/19796 A1 | | 12/1991 |
| WO | WO 1992/03917 A1 | | 3/1992 |
| WO | WO 1992/03918 A1 | | 3/1992 |
| WO | WO 1993/12227 A1 | | 6/1993 |
| WO | WO 1994/02602 A1 | | 2/1994 |
| WO | WO 1994/25585 A1 | | 11/1994 |
| WO | WO 1996/30498 A1 | | 10/1996 |
| WO | WO 1996/33735 A1 | | 10/1996 |
| WO | WO 1996/34096 A1 | | 10/1996 |
| WO | WO 1997/13852 A1 | | 4/1997 |
| WO | WO 1998/24884 A1 | | 6/1998 |
| WO | WO 1998/24893 A1 | | 6/1998 |
| WO | WO 1999/45962 A1 | | 9/1999 |
| WO | WO 2000/26373 A1 | | 5/2000 |
| WO | WO 2000/76310 A1 | | 12/2000 |
| WO | WO 2002/12437 A2 | | 2/2002 |
| WO | WO 2002/43478 A2 | | 6/2002 |
| WO | WO 2002/066630 A1 | | 8/2002 |
| WO | WO 2003/002725 A1 | | 1/2003 |
| WO | WO 2003/027261 A2 | | 4/2003 |
| WO | WO 2003/047336 A2 | | 6/2003 |
| WO | WO 2003/048346 A1 | | 6/2003 |
| WO | WO 2004/076618 A2 | | 9/2004 |
| WO | WO 2004/078937 | | 9/2004 |
| WO | WO 2005/019463 A1 | | 3/2005 |
| WO | WO 2006/072803 A2 | | 7/2006 |
| WO | WO 2006/117699 | * | 11/2006 |
| WO | WO 2007/024715 | | 3/2007 |
| WO | WO 2007/117410 A2 | | 10/2007 |
| WO | WO 2008/027986 A2 | | 3/2008 |
| WO | WO 2008/090958 | | 7/2008 |
| WO | WO 2008/090958 | * | 8/2008 |
| WO | WO 2008/151081 | * | 12/2008 |
| WO | WO 2008/151081 A8 | | 12/2008 |
| WO | WO 2009/143472 A2 | | 11/2009 |
| WO | WO 2009/157771 A2 | | 12/2009 |
| WO | WO 2010/03990 | | 1/2010 |
| WO | WO 2010/039900 A2 | | 4/2010 |
| WO | WO 2010/070263 A1 | | 6/2010 |
| WO | WO 2011/004192 A1 | | 1/2011 |
| WO | WO 2011/123708 | | 10/2011 |
| WO | WO 2011/158009 A1 | | 12/2011 |

OTHER PUBLICATIONS

Mouse platforms jostle for slice of humanized antibody market Nature Biotechnology vol. 31 No. 4 Apr. 2013 pp. 267-269.*
Mice with a human touch 2007, Nature pp. 1075-1077.*
Buchner et al High-resolution mapping of the sodium channel modifier Scnm1 on mouse chromosome 3 and identification of a 1.3-kb recombination hot spot Genomics 82 (2003) 452-459.*
Murphy et al., Unexpected and unexplained phenotypes in transgenic modelsGrowth Hormone & IGF Research 2000, 10, 233-235.*

(56) References Cited

OTHER PUBLICATIONS

Kim et al 1994 Catabolism of the Murine IgGI Molecule: Evidence that Both CH2-CH3 Domain Interfaces are Required for Persistence of IgGl in the Circulation of Mice Scand. J. Immunol., 40:457-465.*
Hafler et al ., J Immunol 1988; 141:131-138;Anti-CD4 and anti-CD2 monoclonal antibody infusions in subjects with multiple sclerosis Immunosuppressive effects and human anti-mouse responses.*
1992, Kappell et al., Current Opinions in Biotechnology, pp. 548-553.*
Houdebine, L, The methods to generate transgenic animals and to control transgene expression(2002, Journal of Biotechnology, vol. 98, p. 145-160) H.*
Cameron, 1977, Recent advances in transgenic technology pp. 253-265.*
Sigmund. Viewpoint: are studies in genetically altered mice out of control? Arterioscler Thromb Vasc Biol. Jun. 2000;20(6):1425-9. Review.S.*
Goldman et al., 2004 (Med Sci Monit, vol. 10, No. 11, RA274-285.*
Vetterman et al Allelic exclusion of mmunoglobulin genes: models and mechanisms Immunological Reviews 2010; pp. 22-42.*
Giraldo et al Size matters: use of YACs, BACs and PACs in transgenic animalsTransgenic Research 10: 83-103, 2001.G.*
Mullins et al .,Transgenesis in nonmurine species Hypertension 1993;22;630-633.*
Afshar et al., "Regulation of IgH Gene Assembly: Role of the Intronic Enhancer and 5 $D_{Q52}$ Region in Targeting $D_HJ_H$ Recombination[1]," J. Immunol. (2006) 176: 2439-2447.
Antibody—Wikipedia, The Free Encyclopedia, Last Visited Jun. 11, 2013.
Askew et al., "Site-Directed Point Mutations in Embryonic Stem Cells: a Gene-Targeting Tag-and-Exchange Strategy," *Molecular and Cellular Biology* 13(7):4115-4124, 1993.
Behringer et al., "Human γ- to β-globin gene switching in transgenic mice," Genes & Development 4:380-389, 1990.
Berman, et al., "Content and organization of the human 19 VH IOCUS: definition of three new VH families and linkage to the Ig CH Locus," The EMBO Journal, 7(3):727-738, 1988.
Blaas et al., "Bacterial artificial chromosomes improve recombinant protein production in mammalian cells," *BMC Biotechnology* 9(3):1-5, 2009.
Bruggeman et al., "A repertoire of monoclonal antibodies with human heavy chains from transgenic mice" PNAS, (1989), 86:6709-6713.
Capecchi, "Generating mice with targeted mutations," *Nature Medicine* 7(10):1086-1090, 2001.
Capecchi, "The New Mouse Genetics: Altering the Genome by Gene Targeting," *Trends in Genetics* 5(3):70-76, 1989.
Carosella, E.D., et. al., "Anti-Human interleukin 2 receptor monoclonal antibody isotypic switching: chimeric rat-human antibodies," *Human Immunology*, 29:233-246, (1990).
Carosella, et al., "Anti-Human Interleukin 2 Receptor Monoclonal Antibody Isotypic Switching: Chimeric Rat-Human Antibodies," Human Immunology, 158:2242-2250; 1997.
Chan et al.,"Epitope mapping of a chimeric CD137 mAb: a necessary step for assessing the biologic relevance of non-human primate models," J Mol Recognit, (2009), 22(3):242-249.
Chen et al. "Immunoglobulin gene rearrangement in B cell deficient mice generated by targeted deletion of the $J_H$ locus," EMBO J., (1993) 12: 821-830.
Chen J., et al. "B cell development in mice that lack one or both immunoglobulin x light chain genes," Int Immunol., Jun. 1993;5(6):647-56.
Combriato and Klobeck,"Regulation of Human Igλ Light Chain Gene Expression by NF-κB[1]." J. Immunol. (2002), 168(3):1259-1266.
Extended European Search Report and Search Opinion for EP2346994, dated Feb. 9, 2012.
Fell et al., "Homologous recombination in hybridoma cells: Heavy chain chimeric antibody produced by gene targeting," *Proc. Natl. Acad. Sci. USA* 86:8507-8511, 1989.

Fishwild et al., "High-avidity humak IgGκ monoclonal antibodies from a novel strain of minilocus transgenic mice," Nat Biotechnol, (1996) 14:845-851.
Frippiat et al. "Organization of the human immunoglobulin lambda light-chain locus on chromosome 22q11.2,"Hum. Mol. Genet. (1995) 4: 983-991.
Hunter, M.J., et al., "Generation of canine-human Fc IgE chimeric antibodies for the determination of the canine IgE domain of interaction with FcεRIα," Molecular Immunology, 45:2262-2268 (2008).
International Preliminary Report on Patentability, for International Application No. PCT/US2009/059131, dated Apr. 5, 2011, 7 pages.
International Search Report, for International Application No. PCT/US2009/059131, dated Jan. 3, 2011, 5 pages.
Jakobovits et al., "Analysis of homozygous mutant chimeric mice: Deletion of the immunoglobulin heavy-chain joining region blocks B-cell development and antibody production," Proc. Natl. Acad. Sci. (1993) 90: 2551-2555.
Janssens et al. "Generation of heavy-chain-only antibodies in mice," Proc. Natl. Acad. Sci. (2006) 103: 15130-15135.
Karreman, "A new set of positive/negative selectable markers for mammalian cells," Gene 218:57-61, 1998.
Kawasaki et al., "The Organization of the Human Immunoglobulin λ Gene Locus," Gen. Res. (1995) 5: 125-135.
Kodumal et al., "Total synthesis of long DNA sequences: Synthesis of a contiguous 32-kb polyketide synthase gene cluster," Proc. Natl. Acad. Sci. (2004), 101:15573-15578.
Lepage et al. "Rapid generation of nested chromosomal deletions on mouse chromosome 2," Proc. Natl. Acad. Sci. (2000) 97: 10471-10476.
Li et al. "Generation of mice with a 200-kb amyloid precursor protein gene deletion by Cre recombinase-mediated site-specific recombination in embryonic stem cells," Proc. Natl. Acad. Sci. (1996) 93: 6158-6162.
Lonberg, "Human antibodies from transgenic animals," *Nature Biotechnology* 23(9):1117-1125, 2005.
Loset et al., "Differential Segmental Flexibility and Reach Dictate the Antigen Binding Mode of Chimeric IgD and IgM: Implications for the Function of the B Cell Receptor," *The Journal of Immunology* 172:2925-2934, 2004.
Lutz et al., "IgD can largely substitute for loss of IgM function in B cells," Nature, (1998), 393:797-801.
Mansour et al., "Disruption of the proto-oncogene int-2 in mouse embryo-derived stem cells: a general strategy for targeting mutations to non-selectable genes," Nature 336:348-352, 1988.
Mendez et al., "Functional transplant of megabase human immunoglobulin loci recapitulates human antibody response in mice," Nature Genetics, (1997), 15(2):146-156.
Nitschke et al. "Immunoglobulin D-deficient mice can mount normal immune responses to thymus-independent and -dependent antigens," Proc. Natl. Acad. Sci. (1993) 90: 1887-1891.
Nissim, et al., "Mapping of the high affinity FeE receptor binding site to the third constant region domain of IgE," The EMBO Journal, 10(1):101-107, 1991.
Pan et al., "Regulation of the promoter for human immunoglobulin γ3 germ-line transcription and its interaction with the 3'α enhancer," Eur. J. Immunol. 30:1019-1029, 2000.
Perlot et al."Elucidation of IgH intronic enhancer functions via germ-line deletion," Proc. Natl. Acad. Sci. (2005) 97: 14362-14367.
Puech et al."Normal cardiovascular development in mice deficient for 16 genes in 550 kb of the velocardiofacial/ DiGeorge syndrome region," Proc. Natl. Acad. Sci. (2000) 97: 10090-10095.
Ramsden and Wu, "Mouse κ light-chain recombination signal sequences mediate recombination more frequently than do those of λ light chain," Proc. Natl. Acad. Sci. (1991) 88: 10721-10725.
Ren et al. "Silencing of the immunoglobulin heavy chain locus by removal of all eight constant-region genes in a 200-kb region," Genomics (2004) 84: 686-695.
Roes and Rajewsky, "Immunoglobulin D (IgD)-deficient Mice Reveal an Auxiliary Receptor Function for IgD in Antigen-mediated Recruitment of B Cells Immunoglobulin D (IgD)-deficient Mice Reveal an Auxiliary Receptor Function for IgD in Antigen-mediated Recruitment of B Cells," J. Exp Med. (1993) 177: 45-55.

(56) References Cited

OTHER PUBLICATIONS

Roux et al., "Flexibility of Human IgG Subclasses," *The Journal of Immunology* 159:3372-3382, 1997.
Selsing et al.,"Immunoglobulin λ Genes," Acad. Press Ltd., (1989) pp. 111-122.
Shizuya et al., "The development and applications of the bacterial artificial chromosome cloning system," *Keio J. Med.* 50(1):26-30, 2001.
Stevenson, G.T., et al., "Conjugation of human Fcγ in closed-hinge or open-hinge configuration to Fab'γ and analogous ligands," Journal of Immunology, 158:2242-2250 (1997).
Strachan and Read, "Genetic manipulation of animals," Human Molecular Genetics, Second Edition. New York: Wiley-Liss, (1999), Chapters 21 and 22.
Tabuchi et al., "Titration of Hepatitis B Virus Infectivity in the Sera of Pre-Acute and Late Acute Phases of HBV Infection: Transmission Experiments to Chimeric Mice With Human Liver Repopulated Hepatocytes," J Med Virol., (2008), 80(12):2064-2068.
Takeda et al., "Deletion of the immunoglobulin χ chain intron enhancer abolishes χ chain gene rearrangement in cis but not λ chain gene rearrangement in trans," EMBO J. (1993) 12: 2329-2336.
Taylor et al., "A transgenic mouse that expresses a diversity of human sequence heavy and light chain immunoglobulins," *Nucleic Acids Research* 20(23):6287-6295, 1992.
Testa et al., "Engineering the mouse genome with bacterial artificial chromosomes to create multipurpose alleles," Nature Biotech. (2003), 21:443-447.
Thomas et al., "High Frequency Targeting of Genes to Specific Sites in the Mammalian Genome," *Cell* 44:419-428, 1986.
Thomas et al., "Site-Directed Mutagenesis by Gene Targeting in Mouse Embryo-Derived Stem Cells," *Cell* 51:503-512, 1987.
Valenzuela et al., "High-through put engineering of the mouse genome coupled with high-resolution expression analysis," Nature Biotech. (2003), 21:652-659.
Venken et al., "P[acman]: A BAC Transgenic Platform for Targeted Insertion of Large DNA Fragments in *D. melanogaster,*" *Science* 314:1747-1751, 2006.
Written Opinion of the International Searching Authority, for International Application No. PCT/US2009/059131, dated Jan. 3, 2011, 6 pages.
Wu et al., "Double replacement: Strategy for efficient introduction of subtle mutations into the murine Colla-1 gene by homologous recombination in embryonic stem cells," *Proc. Natl. Acad. Sci. USA* 91:2819-2823, 1994.
Yang and Seed, "Site-specific gene targeting in mouse embryonic stem cells with intact bacterial artificial chromosomes," Nature Biotech. (2003), 21:447-451.
Zhang et al., "DNA cloning by homologous recombination in *Escherichia coli,*" *Nature Biotechnology* 18:1314-1317, 2000.
Zheng et al., "Engineering Mouse Chromosomes with Cre-loxP: Range, Efficiency, and Somatic Applications" Molec. Cell. Biol. (2000) 20: 648-655.
Zhu et al., "Genomic interval engineering of mice identifies a novel modulator of triglyceride production" Proc. Natl. Acad. Sci. (2000) 97: 1137-1142.
Zou et al., "Block in Development at the Pre-B-II to Immature B Cell Stage in Mice Without Ig and Igλ Light Chain[1]," J. Immunol. (2003) 170: 1354-1361.
Zou et al., "Gene targeting in the Igχ locus: efficient generation of λ chain-expressing B cells, independent of gene rearrangements in Igχ," EMBO J. (1993) 12: 811-820.
Sandin, et al., "Structure and Flexibility of Individual Immunoglobulin G Molecules in Solution," Structure, 12:409-415, 2004.
Torres, et al., "Exchaning Murine and Human Immunoglobulin Constant Chains Affects the Kinetics and Thermodynamics of Antigen Binding and Chimeric Antibody Autoreactivity," PLOS One, 12:1-10, 2007.
Torres, et al., The Immunoglobulin Heavy Chain Constant Region Affects Kinetic and Thermodynamic Parameters of Antibody Variable Region Interactions with Antigen, The Journal of Biochemistry, 282(18):13917-13927, 2007.
Das, S., et al., "Analysis of the Immunoglobulin Light Chain Genes in Zebra Finch: Evolutionary Implications." Molecular Biology and Evolution (2010); 27(1): 113-120.
Extended European Search Report for European Patent Application No. 17178066.1 dated Oct. 12, 2017, 9 pages.
Extended European Search Report for European Patent Application No. 17178088.5 dated Oct. 13, 2017, 9 pages.
Ivics, Z., et al., "Germline transgenesis in pigs by cytoplasmic microinjection of Sleeping Beauty transposons." Nature Protocols (2014); 9: 810-827.
Meng, F., et al., "Optimized production of transgenic buffalo embryos and offspring by cytoplasmic zygote injection." J. Animal Sci. and Biotech. (2015); 6: 44, 7 pages.
Sun, Y., et al., "Immunoglobulin genes and diversity: what we have learned from domestic animals." J. Animal Sci. and Biotech. (2012); 3(18): 1-5.
West and Gill, "Genome editing in large animals." J. Equine Vet. Sci. (2016); 41: 1-6, 12 pages.
Yu, X., et al., "An optimized electrofusion-based protocol for generating virus-specific human monoclonal antibodies." J. Immunol. Methods (2008); 336(2): 142-151.
Chauveau, C., et al., "Synergies between regulatory elements of the immunoglobulin heavy chain locus and its palindromic 3' locus control region." Eur J Immunol. (1998); 28(10): 3048-3056.
Crawley, J.N., "What's Wrong With My Mouse? Behavioral Phenotyping of Transgenic and Knockout Mice." Wiley-Interscience, John Wiley & Sons (2007), pp. 21-29, 12 pages.
Definition of Syngeneic by Merriam-Webster downloaded Aug. 8, 2017; pp. 1-9.
Extended European Search Report and Search Opinion for European Patent Application 11763476.6, dated Sep. 20, 2013, 7 pages.
Felgenhauer, M., et al., "Nucleotide sequences of the cDNAs encoding the V-regions of H- and L-chains of a human monoclonal antibody specific to HIV-1-gp41." Nucleic Acids Res. (1990); 18(16): 4927.
Gama Sosa, M.A., et al., "Animal transgenesis: an overview." Brain Struct Funct (2010); 214: 91-109.
Geier and Schlissel. "Pre-BCR signals and the control of Ig gene rearrangements." Seminars in immunology (2006); 18: 31-39.
Grange and Boyes, "Chromatin opening is tightly linked to enhancer activation at the kappa light chain locus." Biochem Biophys Res Commun. (2007); 363(1): 223-228.
International Preliminary Report on Patentability for PCT/US2011/030823, dated Oct. 11, 2012.
International Search Report and Written Opinion for PCT/US2011/030823, dated Nov. 25, 2011.
Johnson, K., et al., "Regulatory events in early and late B-cell differentiation." Mol Immunol. (2005); 42(7):749-761.
Labrijin, A.F., et al., "Therapeutic IgG4 antibodies engage in Fab-arm exchange with endogenous human IgG4 in vivo." Nat Biotechnol. (2009); 27(8): 767-771, 7 pages.
Lefranc, M.P., "Nomenclature of the human immunoglobulin genes." Curr Protoc Immunol. (2000); Supplement 40, pp. 1-37.
Lightle, S., et al., "Mutations within a human IgG2 antibody form distinct and homogeneous disulfide isomers but do not affect Fc gamma receptor or C1q binding." Protein Science (2010); 19(4): 753-762.
Manis, J.P., et al., "Class Switching in B Cells Lacking 3' Immunoglobulin Heavy Chain Enhancers." The Journal of Experimental Medicine (1998); 188(8): 1421, pp. 1-27.
Pruzina, et al., "Human monoclonal antibodies to HIV-1 gp 140 from mice bearing YAC-based human immunoglobulin transloci," Protein Engineering, Design & Selection, 24(10):791-799 (2011).
Reddy, M.P., et al., "Elimination of Fc receptor-dependent effector functions of a modified IgG4 monoclonal antibody to human CD4." J Immunol. (2000); 164(4): 1925-1933.
Ristevski, S., "Making better transgenic models: conditional, temporal, and spatial approaches." Molecular Biotechnology (2005); 29(2): 153-163.

(56) References Cited

OTHER PUBLICATIONS

Roitt, I., et al., Essential Immunology, Ch. 3, Sixth Edition, Blackwell Scientific Publications (1988); pp. 31-35.
Roopenian and Akilesh, "FcRn: the neonatal Fc receptor comes of age." Nature Reviews. Immunology (2007); 7: 715-25.
Salfeld, J.G., "Isotype selection in antibody engineering." Nature Biotechnology (2007); 25: 1369-1372.
Schuurman, J., et al., "The inter-heavy chain disulfide bonds of IgG4 are in equilibrium with intra-chain disulfide bonds." Mol Immunol. (2001); 38(1): 1-8.
Sigmund, C.D., "Viewpoint: are studies in genetically altered mice out of control?" Arterioscler. Thromb. Vasc. Biol. (2000); 20(6): 1425-1429.
Smith, K.R., "Gene transfer in higher animals: theoretical considerations and key." Journal of Biotechnology (2002); 99: 1-22.
Vettermann and Schlissel, "Allelic exclusion of immunoglobulin genes: models and mechanisms." Immunol Rev. (2010); 237(1): 22-42.
Xu, Y., et al. "Deletion of the Igκ light chain intronic enhancer/matrix attachment region impairs but does not abolish VκJκ rearrangement." Immunity (1996); 4(4): 377-385.
Yang and Ross, Genetic Modification of Domestic Animals for Agriculture and Biomedical applications, Biomedical Science, Engineering and Technology; Prof Dhanjoo Ghista (Ed) in Tech Publisher (2012); pp. 699-726.
Pradhan and Majumdar, "An Efficient Method for Generation of Transgenic Rats Avoiding Embryo Manipulation." Molecular Therapy—Nucleic Acids (2016); 5: e293, 11 pages.
Briere, et al, "Human interleukin 10 induces naive surface immunoglobulin D+ (sIgD+) B cells to secrete IgG1 and IgG3," Journal of Experimental Medicine, 179(2):757-762 (1994).
Krawinkel, et al., Comparison of the hinge-coding segments in human immunoglobulin gamma heavy chain genes and the linkage of the gamma 2 and gamma 4 subclass genes, EMBO Journal, 1(4):403-407 (1982).
Barthold, "Genetically altered mice: phenotypes, no phenotypes, and Faux phenotypes," Genetica, 122:75-88 (2004).
Brevini, et al., "No shortcuts to pig embryonic stem cells," Theriogenology, 74(4):544-550 (2010).
Buta, et al., "Reconsidering pluripotency tests: do we still need teratoma assays?," Stem Cell Research, 11:552-562 (2013).
Garcia-Arocena, The Jackson Laboratory, "Same Mutation, Different Phenotype?", (2014) (5 pages).
Gomez, et al., "Derivation of cat embryonic stem-like cells from in vitro-produced blastocysts on homologous and heterologous feeder cells," Theriogenology, 74:498-515 (2010).
Grunberg, et al., "High-yield production of recombinant antibody fragments in HEK-293 cells using sodium butyrate," BioTechniques, 34(5):968-972 (2003).
Heiman-Patterson, et al., "Effect of genetic background on phenotype variability in transgenic mouse models of amyotrophic lateral sclerosis: a window of opportunity in the search for genetic modifiers," Amyotrophic Lateral Schlerosis, 12:79-86 (2011).
Hong, et al., "Derivation and characterization of embryonic stem cells lines derived from transgenic Fischer 344 and Dark Agouti rats," Stem Cells and Dev., 21(9):1571-1586 (2012).
Munoz, et al., "Conventional pluripotency markers are unspecific for bovine embryonic-derived cell-lines.," Theriogenology, 69(9):1159-1164 (2008).
Paris, et al., "Equine embryos and embryonic stem cells: defining reliable markers of pluripotency.," Theriogenology(4), 74:516-524 (2010).
Popov, et al., "A human immunoglobulin lambda locus is similarly well expressed in mice and humans," Journal of Experimental Medicine, 189(10):1611-1619 (1999).
Tong, et al., "Production of p53 gene knockout rats by homologous recombination in embryonic stem cells," Nature, 467(7312):211-213 (2010).
Brekke, et al., "The structural requirements for complement activation by IgG: does it hinge on the hinge?" Immunology Today (1995); 16(2): 85-90.
Burton, et al., New Comprehensive Biochemistry vol. 17, 1987, pp. 1-50 Chapter 1 Structure and function of antibodies, 52 pages.
Hafler et al., "Anti-CD4 and anti-CD2 monoclonal antibody infusions in subjects with multiple sclerosis. Immunosuppressive effects and human anti-mouse responses." J Immunol (1988); 141(1): 131-138.

\* cited by examiner

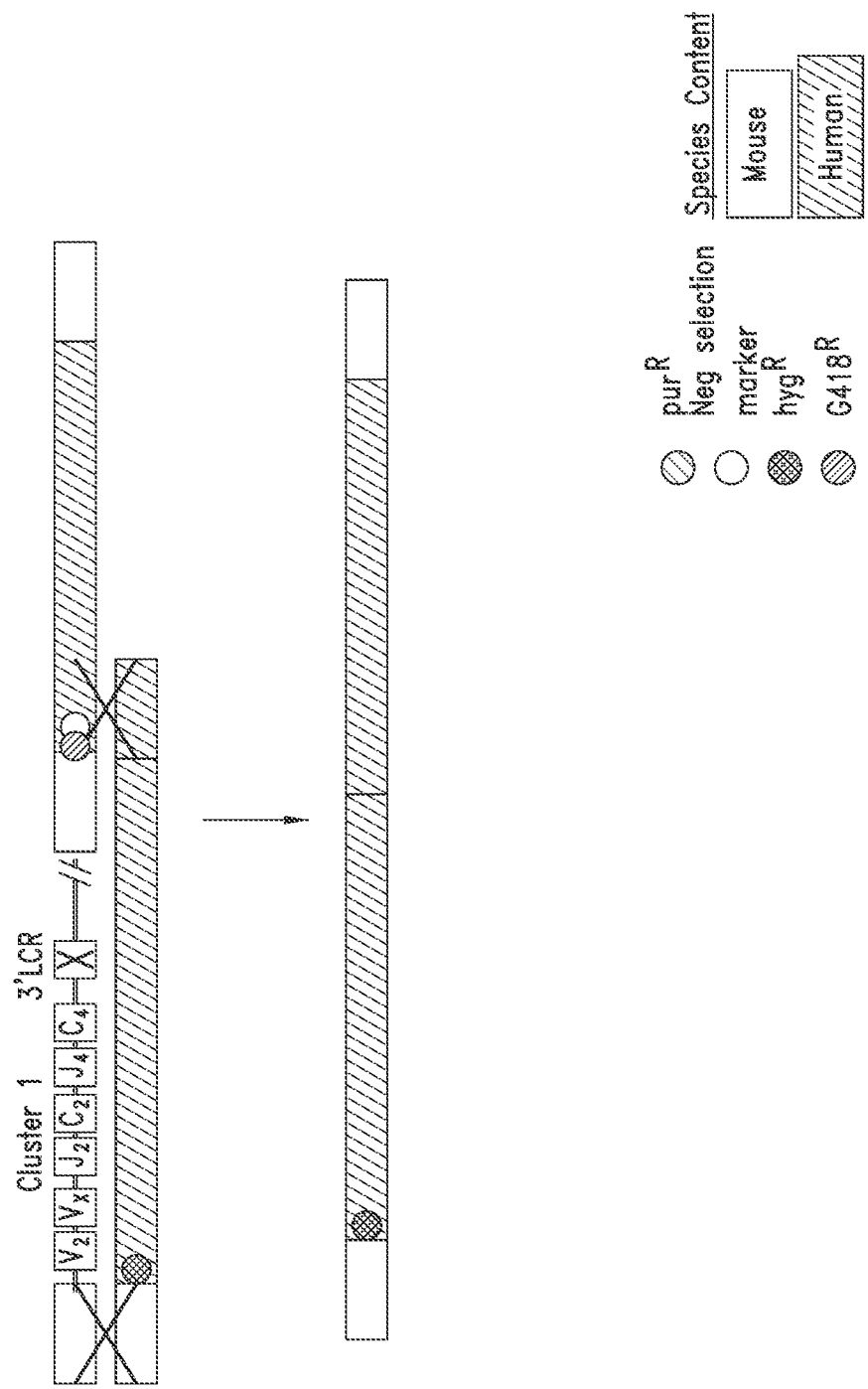

NON-HUMAN MAMMALS FOR THE PRODUCTION OF CHIMERIC ANTIBODIES

CROSS-REFERENCE TO RELATED APPLICATION

This application is a divisional of U.S. patent application Ser. No. 13/121,883, filed Jun. 9, 2011, now U.S. Pat. No. 9,346,873, which is a U.S. National stage application filed tinder 35 § 371 of international Patent Application No, PCT/US2009/059131, accorded an international filing date of Sep. 30, 2009, which claims the benefit under 35 U.S.C. 119(e) of U.S. Provisional Patent Application No. 61/101,938 flied Oct. 1, 2008 and U.S. Provisional Patent Application No. 61/101,597 filed Sep. 30, 2008, where these applications are incorporated herein by reference in their entireties.

BACKGROUND

Technical Field

The present invention is directed generally to the production of knock-in non-human mammals and cells and chimeric immunoglobulin chains and antibodies.

Description of the Related Art

Disease therapies utilizing monoclonal antibodies (mAbs) have revolutionized medicine, and mAb-based drugs are now utilized in the treatment of cancer, autoimmunity, inflammation, macular degeneration, infections, etc. However, the available technologies for generation and discovery of mAbs for use in the prevention and treatment of diseases and disorders have significant drawbacks including inefficiency, absence or loss of sufficient potency, absence or loss of specificity and the induction of an immune response against the therapeutic mAb. The first attempts to use mAbs as therapeutics were hindered by the immunogenicity of the mouse amino acid composition of the mAbs. When administered to humans, the mouse amino acid sequence elicited a human anti-mouse antibody (HAMA) response that dramatically reduced the potency and pharmacokinetics of the drug as well as causing severe and potentially fatal allergic reactions.

Additional methods to generate mAb therapeutics include chimerized mAbs (cmAbs) created through recombinant DNA technology combining a mouse-derived variable domain appended to a human constant region. Other methods of generating antibodies involve humanizing mAbs in vitro to further reduce the amount of mouse amino acid sequence in a therapeutic mAb. Antibody-display technologies developed to generate "fully-human" antibodies in vitro have yet to adequately mimic the natural antibody maturation process that occurs during an in vivo immune response (see pg. 1122-23, Lonberg, Nat. Biotech. (2005) 23:1117-1125.) mAbs developed using these methods can elicit an immune response that can reduce efficacy and/or be life-threatening, and they are typically a time-consuming and costly process. Also, during the molecular processes inherent in these methods, loss of affinity and epitope shifting can occur, thereby reducing potency and introducing undesirable changes in specificity.

Transgenic mice have been engineered to produce fully human antibodies by introducing human antibody transgenes to functionally replace inactivated mouse immunoglobulin (Ig) loci. However, many of these transgenic mouse models lack important components in the antibody development process, such as sufficient diversity in the genes from which antibody variable regions are generated, the ability to make IgD (Loset et al., *J. Immunol.*, (2004) 172:2925-2934), important cis regulatory elements important for class switch recombination (CSR), or a fully functional 3' locus control region (LCR) (e.g., U.S. Pat. No. 7,049,426; and Pan et al., *Eur. J. Immunol.* (2000) 30:1019-1029). Some transgenic mice contain yeast artificial chromosomes or human miniloci as integrated transgenes. Others carry transchromosomes that exhibit various frequencies of mitotic and meiotic instability. Furthermore, the fully human constant regions of these transgenic mice function sub-optimally due to reduced activity in conjunction with other endogenous and trans-acting components of the BCR signal transduction apparatus, e.g., Igα and Igβ, and Fc receptors (FcR), as compared to normal mice.

Mice have also been genetically engineered to produce chimeric antibodies that are composed of human V domains appended to mouse C domains that remain fully intact, with the fully-intact and modified portions including all genomic DNA downstream of the J gene cluster (see U.S. Pat. Nos. 5,770,429 and 6,596,541 and U.S. Patent Application Publication No. 2007/0061900). Human V regions from these mice can be recovered and appended to human constant region genes by molecular biological methods and expressed by recombinant methods to produce fully-human antibodies. The antibodies from these mice may exhibit reduction or loss of activity, potency, solubility etc. when the human V region is removed from the context of the mouse C domains with which it was evolved and then appended to a human C region to make a fully human antibody.

Current methods of developing a therapeutic mAb can alter functions of the antibody, such as solubility, potency and antigen specificity, which were selected for during initial stages development. In addition, mAbs generated by current methods have the potential to elicit a dangerous immune response upon administration. Current human and chimeric antibody producing mice lack appropriate genetic content to function properly, e.g., genetic diversity, cis regulatory elements, trans acting regulatory elements, signaling domains, genetic stability. It would be beneficial to develop methods and compositions for the enhanced generation and discovery of therapeutic antibodies and that retain potency and specificity through the antibody generation, discovery, development, and production process without eliciting an immune response, as well as methods of producing such antibodies. The present invention provides a solution for generating such antibodies in transgenic animals.

BRIEF SUMMARY

The present invention relates to knock-in non-human mammals and cells, antibodies, methods, compositions (including pharmaceutical compositions) as well as kits of various embodiments disclosed herein. More specifically, the present invention relates to methods, compositions and kits relating to chimeric Ig chains and antibodies produced by the knock-in non-human mammals and cells and the human antibodies and fragments thereof engineered from the variable domains of said chimeric antibodies.

Some aspects of the invention relate to a homologous recombination competent non-human mammalian cell having a genome comprising (1) a human VH gene segment and (2) a portion of a syngeneic Ig heavy chain locus comprising all or a part of gene segments downstream of JH wherein a syngeneic CH1 domain is replaced with a human CH1 domain and wherein the human VH gene segment and the syngeneic Ig heavy chain locus replace an endogenous Ig heavy chain, or a portion thereof, so that the cell comprises a genome encoding a chimeric Ig heavy chain. In certain embodiments, the portion further comprises a 3' locus control region (LCR), or a functional fragment thereof. In one embodiment, the cell further comprises a human DH gene segment. In another embodiment, the cell further comprises a DH gene segment from a mammal. In a particular embodiment, the DH gene segment is selected from the group consisting of human, non-human primate, rabbit, sheep, rat, hamster, and mouse. In particular embodiments, the DH gene segment is human. In another embodiment, the human CH1 domain comprises a single CH gene segment, e.g., Cγ1, Cγ2, and Cγ4.

In yet another embodiment, the cell further comprises a human upper hinge gene segment. In a related embodiment, the cell further comprises a human middle hinge gene segment. In particular embodiments, the human hinge gene segment is an IgG4 hinge gene segment. In some embodiments, serine is substituted for the proline at position 229. In certain preferred embodiments, the chimeric Ig heavy chain is capable of binding an endogenous FcR.

In certain embodiments, the cell is an embryonic stem cell. In another embodiment, the cell is a mouse cell.

Another aspect of the invention relates to a method of producing the cell described above that comprises a genome encoding a chimeric Ig heavy chain comprising the steps of producing a first BAC comprising a human VH gene segment; producing a second BAC comprising a portion of a syngeneic Ig heavy chain locus comprising all or a part of the gene segments downstream of JH, wherein a syngeneic CH1 domain is replaced with a human CH1 domain; introducing the first BAC into a homologous recombination competent non-human mammalian cell and replacing all or a portion of an endogenous VH gene segment via homologous recombination; and introducing the second BAC into the cell and replacing all or a portion of an endogenous Ig heavy chain locus via homologous recombination, so that the cell comprises a genome encoding a chimeric Ig heavy chain. In one embodiment, either the first or second BAC further comprises a human JH gene segment.

In particular embodiments, the first BAC further comprises a first site-specific recombinase recognition sequence near the 3' end of the first BAC, and the second BAC further comprises a second site-specific recombinase recognition sequence near the 5' end of the second BAC. A related embodiment further comprises the step of expressing a site-specific recombinase, wherein an intervening sequence between the first and second site-specific recombinase recognition sequences is removed. In a particular embodiment, the first and second site-specific recombinase recognition sequences are loxP or variants thereof, and the site-specific recombinase is CRE. In another embodiment, the first and second site-specific recombinase recognition sequences are frt, and the site-specific recombinase is flp.

In certain embodiments related to a method for producing the cell according to the invention, the introducing step of the second BAC occurs before the introducing step of the first BAC.

Some aspects of the invention relate to a homologous recombination competent non-human mammalian cell having a genome comprising a human Ig light chain locus, or a portion thereof, wherein the human Ig light chain locus replaces all or a portion of an endogenous Ig light chain locus, so that the cell comprises a genome encoding a human Ig light chain, or a portion thereof. In one embodiment, the human Ig light chain locus comprises a human Igκ variable region. In a related embodiment, the Ig light chain locus further comprises a human Igκ constant region.

In yet another embodiment, the human Ig light chain locus comprises all or a portion of a human Igλ light chain locus and an Igλ 3'LCR, or a functional fragment thereof. In one embodiment, the human Igλ light chain locus comprises the entire human Igλ locus. In another embodiment the human Igλ light chain locus comprises human Vλ gene segments and 1 to 7 Jλ-Cλ gene segment pairs, wherein the human Cλ is replaced with syngeneic Cλ. In yet another embodiment, the human Igλ light chain locus comprises human Vλ gene segments, 1 to 7 human Jλ gene segments, and a single human Cλ gene segment, wherein the human gene segments resemble a human Igλ locus configuration. In particular embodiments, the Igλ 3' LCR, or a functional fragment thereof, is from a mammal selected from the group consisting of human, non-human primate, and rat. In one embodiment the Igλ 3' LCR, or a functional fragment thereof, is human. In particular embodiments, the Igλ 3' LCR, or a functional fragment thereof, binds NFκb. In one embodiment, the Igλ 3' LCR, or a functional fragment thereof, is from mouse and has been mutagenized so as to restore binding of NFκb. In other embodiments, the 3' LCR, or a functional fragment thereof, in the human Igλ locus is an Igκ 3' LCR, or functional fragment thereof.

In certain embodiments, the cell is an embryonic stem cell. In another embodiment, the cell is a mouse cell.

Another aspect of the invention relates to a method of producing the cell described above that comprises a genome encoding a human Ig light chain, or a portion thereof, comprising the steps of producing a first BAC comprising a human Ig light chain locus, or a portion thereof; introducing the first BAC into a homologous recombination competent non-human mammalian cell; and replacing an endogenous Ig light chain locus, or a portion thereof, via homologous recombination, so that the cell comprises a genome encoding a human Ig light chain, or a portion thereof.

In particular embodiments, the human Ig light chain locus comprises a human Igκ variable region. A related embodiment further comprises the steps of producing a second BAC comprising a human Igκ constant region; introducing the second BAC into the cell; and replacing all or a portion of an endogenous Igκ constant region.

In yet another embodiment, the first BAC further comprises a first site-specific recombinase recognition sequence near the 3' end of the first BAC, and the second BAC further comprises a second site-specific recombinase recognition sequence near the 5' end of the second BAC. In a related embodiment, the method further comprises the step of expressing a site-specific recombinase, wherein an intervening sequence between the first and second site-specific recombinase recognition sequences is removed. In a particular embodiment, the first and second site-specific recombinase recognition sequences are loxP or variants thereof, and the site-specific recombinase is CRE. In another embodiment, the first and second site-specific recombinase recognition sequences are frt, and the site-specific recombinase is flp.

In certain embodiments related to a method for producing the cell according to the invention, the introducing step of the second BAC occurs before the introducing step of the first BAC.

In certain embodiments, the human Ig light chain locus comprises all or a portion of a human Igλ light chain locus and an Igλ 3'LCR, or a functional fragment thereof. In one embodiment, the human Igλ light chain locus comprises a human Igλ light chain variable region. A related embodiment further comprises the steps of producing a second BAC comprising a human Igλ constant region; introducing the second BAC into the cell; and replacing all or a portion of an endogenous Igλ constant region. In some embodiments, the first BAC further comprises a first site-specific recombinase recognition sequence near the 3' end of the first BAC, and the second BAC further comprises a second site-specific recombinase recognition sequence near the 5' end of the second BAC. In a related embodiment, the method further comprises the step of expressing a site-specific recombinase, wherein an intervening sequence between the first and second site-specific recombinase recognition sequences is removed. In a particular embodiment, the first and second site-specific recombinase recognition sequences are loxP or variants thereof, and the site-specific recombinase is CRE. In another embodiment, the first and second site-specific recombinase recognition sequences are frt, and the site-specific recombinase is flp.

In certain embodiments, the human Igλ light chain locus comprises human Vλ gene segments and 1 to 7 Jλ-Cλ gene segment pairs, wherein the human Cλ is replaced with syngeneic Cλ. In yet another embodiment, the human Igλ light chain locus comprises human Vλ gene segments, 1 to 7 human Jλ gene segments, and a single human Cλ gene segment, wherein said human gene segments resemble a human Igλ locus configuration. A related method further comprises confirming the incorporation of splice sequences into the BAC, and incorporating the splice sequences if not already incorporated into the BAC, prior to the introducing step.

In one embodiment, the human Vλ gene segments comprise cluster A. A related embodiment further comprises the steps of producing a second BAC comprising cluster B human Vλ gene segments; introducing the second BAC into said cell; and replacing endogenous Vλ gene segments. In a further embodiment, the second BAC further comprises human cluster C Vλ gene segments.

Some aspects of the invention relate to a homologous recombination competent non-human mammalian cell having a genome comprising (1) a human Ig locus, or a portion thereof, and (2) a cluster of human FcR genes, wherein the human Ig locus and FcR genes replace the endogenous regions, and wherein the genome encodes a human Ig chain, or a portion thereof, and a human FcR. In particular embodiments, the human Ig locus comprises a portion of a human Ig heavy chain locus comprising all or a part of the gene segments downstream of JH, such that the portion of a human Ig heavy chain engages a human FcR. In certain embodiments, the cell is a non-human embryonic stem cell. In other embodiments, the cell is a mouse cell.

Certain aspects of the invention relate to a method of producing the cell described above that has a genome encodes a human Ig chain, or a portion thereof, and a human FcR comprising the steps of producing a first BAC comprising a human Ig locus, or a portion thereof; producing a second BAC comprising a cluster of human FcR genes; introducing the first BAC into a homologous recombination competent non-human mammalian cell and replacing all or a portion of an endogenous Ig locus via homologous recombination; and introducing the second BAC into said cell and replacing an endogenous cluster of FcR genes via homologous recombination, so that the cell comprises a genome encoding a human Ig chain, or a portion thereof, and a human FcR.

Another aspect of the invention relates to a knock-in non-human mammal having a genome comprising (1) a human VH gene segment and (2) a portion of a syngeneic Ig heavy chain locus comprising all or a part of gene segments downstream of JH wherein a syngeneic CH1 domain is replaced with a human CH1 domain; and wherein the human VH gene segment and the syngeneic Ig heavy chain locus replace all or a portion of an endogenous Ig heavy chain locus, so that the mammal is capable of producing a chimeric Ig heavy chain.

In one embodiment, the mammal further comprises a human JH gene segment. In certain embodiments, the portion further comprises a 3' locus control region (LCR), or a functional fragment thereof. In another embodiment, the mammal further comprises a DH gene segment from a mammal. In a particular embodiment, the DH gene segment is selected from the group consisting of human, non-human primate, rabbit, sheep, rat, hamster, and mouse. In particular embodiments, the DH gene segment is human. In another embodiment, the human CH1 domain comprises a single CH gene segment, e.g., Cγ1, Cγ2, and Cγ4.

In yet another embodiment, the mammal further comprises a human upper hinge gene segment. In a related embodiment, the cell further comprises a human middle hinge gene segment. In particular embodiments, the human hinge gene segment is an IgG4 hinge gene segment. In some embodiments, serine is substituted for the proline at position 229. In certain preferred embodiments, the chimeric Ig heavy chain is capable of binding an endogenous FcR.

Yet another aspect of the invention relates to a knock-in non-human mammal having a genome comprising a human Ig light chain locus, or a portion thereof, wherein said human Ig light chain locus replaces all or a portion of an endogenous Ig light chain locus, such that said mammal is capable of producing a human Ig light chain, or a portion thereof.

In one embodiment, the human Ig light chain locus comprises a human Igκ variable region. In a related embodiment, the Ig light chain locus further comprises a human Igκ constant region.

In yet another embodiment, the human Ig light chain locus comprises all or a portion of a human Igλ light chain locus and an Igλ 3'LCR, or a functional fragment thereof. In one embodiment, the human Igλ light chain locus comprises the entire human Igλ locus. In another embodiment the human Igλ light chain locus comprises human Vλ gene segments and 1 to 7 Jλ-Cλ gene segment pairs, wherein the human Cλ is replaced with syngeneic Cλ. In yet another embodiment, the human Igλ light chain locus comprises human Vλ gene segments, 1 to 7 human Jλ gene segments, and a single human Cλ gene segment, wherein the human gene segments resemble a human Igλ locus configuration. In a related embodiment, the chimeric antibody rearranges and expresses, resulting in a representation of Igλ relative to Igκ greater than 40:60. In particular embodiments, the Igλ 3' LCR, or a functional fragment thereof, is from a mammal selected from the group consisting of human, non-human primate, and rat. In one embodiment the Igλ 3' LCR, or a functional fragment thereof, is human. In particular embodiments, the Igλ 3' LCR, or a functional fragment thereof, binds NFκb. In one embodiment, the Igλ 3' LCR, or a functional fragment thereof, is from mouse and has been mutagenized so as to restore binding of NFκb. In other embodiments, the 3' LCR, or a functional fragment thereof, in the human Igλ locus is an Igκ 3' LCR, or functional fragment thereof.

In certain embodiments, the knock-in non-human mammal capable of producing a chimeric Ig heavy chain described above further comprises a human Ig light chain locus, or a portion thereof, wherein the human Ig light chain locus replaces all or a portion of an endogenous Ig light chain locus.

Another aspect of the invention provides a knock-in non-human mammal having a genome comprising (1) a human Ig locus, or a portion thereof, and (2) a cluster of human FcR genes, wherein the human Ig locus and FcR genes replace the orthologous endogenous regions, and wherein the mammal is capable of producing a human Ig chain, or a portion thereof, and a human FcR. In one embodiment, the human Ig locus comprises a portion of a human Ig heavy chain locus, said portion comprising all or a part of the gene segments downstream of JH, such that said Ig heavy chain engages a human FcR. In a related embodiment, the human Ig heavy chain locus further comprises all or a part of a human variable region. In yet another embodiment, the mammal further comprises a human Ig light chain locus, or a portion thereof, wherein said human Ig light chain locus replaces an endogenous Ig light chain locus, or a portion thereof, such that the knock-in non-human mammal is capable of producing a human antibody and a human FcR.

In particular embodiments, the knock-in non-human mammal according to the invention is a mouse.

Another embodiment relates to an antibody produced by the knock-in non-human mammal according to the invention, wherein said antibody comprises a human Ig heavy or light chain, or a portion thereof. One embodiment provides a method of producing an antibody that specifically binds to a target antigen comprising immunizing a knock-in non-human mammal according to the invention with the target antigen and recovering the antibody that comprises a human Ig heavy or light chain, or a portion thereof.

Yet another embodiment provides a method of detecting a target antigen comprising detecting an antibody according to the invention with a secondary detection agent that recognizes a portion of the antibody. In related embodiments, the portion comprises the Fc region of the antibody, a CH1 domain, a CH2 domain, a CH3 domain, the Fab domain of the antibody, the $F(ab')_2$ domain of the antibody, a Cκ domain, or a Cλ domain of the antibody. In another embodiment, the method further comprises evaluating tissue distribution of said target antigen.

Certain embodiments relate to a pharmaceutical composition comprising the antibody according to the invention and a pharmaceutically acceptable carrier. In another embodiment, a kit comprises the antibody according to the invention and instructions for use of said antibody.

Another aspect of the invention relates to a humanized antibody encoded by a polynucleotide sequence comprising (1) a polynucleotide sequence encoding the human gene segments of the antibody according to the invention appended to (2) a polynucleotide sequence encoding the remaining portion of a human constant region. In one embodiment, the human gene segments comprise human V region gene segments. In another embodiment, a pharmaceutical composition comprises the humanized antibody and a pharmaceutically acceptable carrier. In yet another embodiment, a kit comprises the humanized antibody and instructions for use of said antibody.

Yet another aspect of the invention relates to a method of producing the mammal capable of producing a chimeric Ig heavy chain described above comprising the steps of producing a first BAC comprising a human VH gene segment; producing a second BAC comprising a portion of a syngeneic Ig heavy chain locus comprising all or a part of gene segments downstream of JH, wherein a syngeneic CH1 domain is replaced with a human CH1 domain; introducing the first BAC into a homologous recombination competent non-human mammalian cell and replacing an endogenous VH gene segment via homologous recombination; introducing the second BAC into said cell and replacing all or a portion of an endogenous Ig heavy chain locus via homologous recombination; and generating from the cell a knock-in non-human mammal capable of producing a chimeric Ig heavy chain. In one embodiment, either the first or second BAC further comprises a human JH gene segment. In certain embodiments, the generating step comprises blastocyst microinjection, morula aggregation, or somatic cell nuclear transfer.

Another aspect of the invention relates to a method of producing the mammal capable of producing a human Ig light chain described above comprising the steps of producing a first BAC comprising a human Ig light chain locus, or a portion thereof; introducing the first BAC into a homologous recombination competent non-human mammalian cell and replacing all or a portion of an orthologous endogenous Ig light chain locus via homologous recombination; and generating from the cell a knock-in non-human mammal capable of producing a human Ig light chain, or a portion thereof.

In certain embodiments, the human Ig light chain locus comprises an Igκ variable region. A further embodiment comprises the steps of producing a second BAC comprising a human Igκ constant region; introducing the second BAC into the cell; and replacing all or a portion of an endogenous Igκ constant region.

In certain embodiments related to a method for producing the mammal according to the invention, the introducing step of the second BAC occurs before the introducing step of the first BAC.

In one embodiment, the human Ig light chain locus comprises all or a portion of a human Igλ light chain locus and an Igλ 3'LCR, or a functional fragment thereof, replacing an orthologous endogenous Igλ locus and 3' LCR via homologous recombination. In a related embodiment, the Igλ is expressed at about a ratio of 40:60 relative to Igκ. In yet another embodiment, the human Igλ light chain locus comprises the entire human Igλ locus. In another embodiment, the human Igλ light chain locus comprises human Vλ gene segments and 1 to 7 Jλ-Cλ gene segment pairs, wherein the human Cλ is replaced with syngeneic Cλ.

In one embodiment, the human Igλ light chain locus comprises the human Vλ gene segments, 1 to 7 Jλ gene segments, and a single Cλ gene segment, wherein the gene segments are reconstructed to resemble human Igλ configuration. In a related embodiment, the method further comprises confirming the incorporation of splice sequences into the BAC, and incorporating the splice sequences if not already incorporated into the BAC, prior to the introducing step.

In another embodiment Igλ locus rearranges efficiently, resulting in a higher representation of Igλ relative to Igκ greater than 40:60. In one embodiment, the human Vλ gene segments comprise cluster A. A related embodiment further comprises the steps of producing a second BAC comprising cluster B human Vλ gene segments; introducing the second BAC into the cell; and replacing endogenous Vλ gene segments. In another related embodiment, the second BAC further comprises human cluster C Vλ gene segments.

One aspect of the invention relates to a method for producing a knock-in non-human mammal that is capable of producing a chimeric Ig heavy chain and a human Ig light chain comprising the steps of breeding a non-human mammal comprising a chimeric Ig heavy chain locus, wherein the Ig heavy chain locus comprises (1) a human VH gene segment and (2) a portion of a syngeneic Ig heavy chain locus comprising all or a part of gene segments downstream of JH, wherein a syngeneic CH1 domain is replaced with a human CH1 domain, with a non-human mammal comprising a human Ig light chain locus; selecting offspring having a genome comprising the chimeric Ig heavy chain locus and the human Ig light chain locus; further breeding the offspring; and producing offspring having a genome homozygous for the chimeric heavy chain and human light chain loci.

One embodiment of the invention relates to a method for producing the mammal capable of producing a human Ig chain, or a portion thereof, and a human FcR described above comprising the steps of producing a first BAC comprising a human Ig locus, or a portion thereof; producing a second BAC comprising a cluster of human FcR genes; introducing the first BAC into a homologous recombination competent non-human mammalian cell and replacing all or a portion of an endogenous Ig locus via homologous recombination; introducing the second BAC into said cell and replacing all or a portion of an endogenous cluster of FcR genes via homologous recombination; and generating from the cell a knock-in non-human mammal comprising a genome that encodes a human Ig chain, or a portion thereof, and a human FcR. In a related embodiment, the human Ig locus comprises a portion of an Ig heavy chain locus, said portion comprising all or a part of the gene segments downstream of JH, such that said Ig heavy chain engages a human FcR.

Another aspect of the invention provides a method for producing a knock-in non-human mammal capable of producing a human antibody, wherein the antibody engages a human FcR, comprising the steps of producing a first BAC comprising a human Ig heavy chain locus, a second BAC comprising a human Ig light chain locus, and a third BAC comprising a cluster of human FcR gene segments; introducing the first, second and third BACs sequentially into a homologous recombination competent non-human mammalian cell and replacing an endogenous Ig heavy, Ig light, and FcR gene segment cluster, respectively, via homologous recombination; and generating from the cell a knock-in non-human mammal capable of producing a human antibody.

Yet another embodiment relates to a method for producing a knock-in non-human mammal that is capable of producing a human antibody and a human FcR comprising the steps of breeding a non-human mammal comprising a human Ig heavy chain locus, wherein said Ig heavy chain locus comprises all or a part of the human gene segments downstream of JH, with a non-human mammal comprising a human Ig light chain locus; selecting offspring having a genome comprising the human Ig heavy chain locus and the human Ig light chain locus; further breeding the offspring; and producing offspring having a genome homozygous for the human heavy and light chain loci.

BRIEF DESCRIPTION OF THE SEVERAL VIEWS OF THE DRAWINGS

FIG. 1A, FIG. 1B, and FIG. 1C are diagrams that show stage 1, stage 2, and stage 3, respectively, of selection and screening steps during the homologous recombination process of an IgH locus.

FIG. 2A and FIG. 2B are diagrams that show stage 1 and stage 2, respectively, of selection and screening steps during the homologous recombination of an Igκ locus.

FIG. 3A and FIG. 3B are diagrams that show stage 1 and stage 2, respectively, of selection and screening steps during the homologous recombination process of an Igλ locus.

FIG. 6B is a diagram that shows the introduction of a second BAC into the mouse Igλ locus that homologously recombines with a portion of the first BAC and a portion of the endogenous mouse Igλ locus.

DETAILED DESCRIPTION

Overview

Figure 1A:
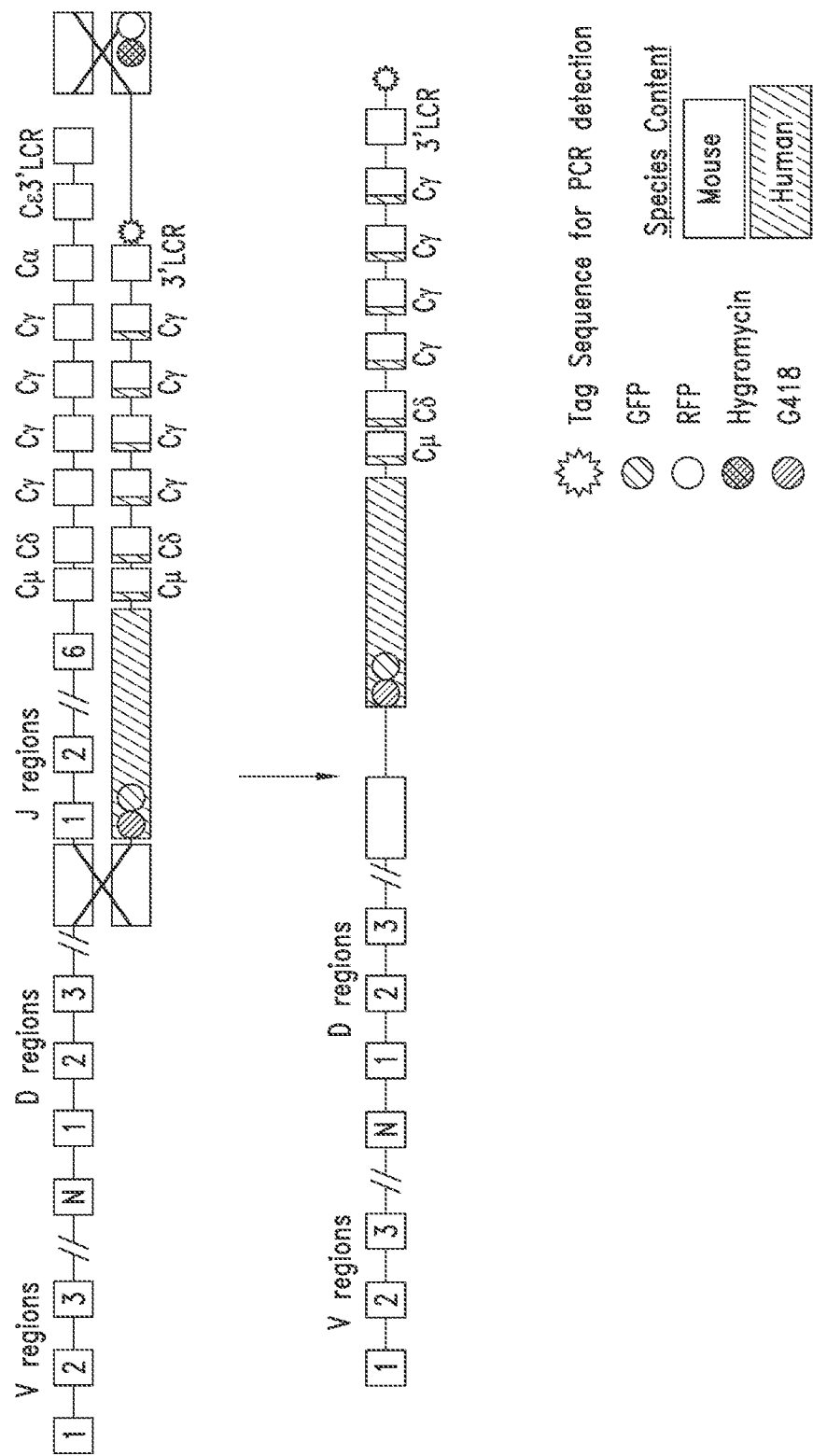
FIGS. 1A-1C depict the introduction of a chimeric Ig heavy chain via sequential homologous recombination steps.

The present invention includes knock-in non-human mammals that produce chimeric or humanized antibodies, methods of producing such knock-in non-human cells and mammals, and compositions and kits comprising the antibodies produced thereby.

Specifically, embodiments of the invention provide chimeric-antibody producing non-human mammals and cells and methods of producing the mammals and cells. In antibody producing mammals, the endogenous immunoglobulin (Ig) V, (D) and J genes are replaced by their human orthologs using homologous recombination in embryonic stem cells by methods described herein, such as using BACs carrying large portions of the human V, D and J genes and flanked by appropriate homology targeting DNA so as to facilitate high-frequency homologous recombination into the endogenous IgH locus. This can be done in a single replacement in each Ig locus, by sequential ("walking") replacement, or by replacing portions of the locus followed by removing intervening sequences. A BAC carrying all or part of the IgH locus downstream of JH can be engineered so that in each constant region gene, the endogenous CH1 domain is replaced with a human CH1 domain using the ability to make very precise modifications of DNA carried in BACs in E. coli. Alternatively, a BAC carrying all or part of the IgH locus downstream of JH can be engineered so that in each constant region gene, the endogenous CH1 domain is replaced with a human CH1 domain, using the ability to precisely synthesize and assemble DNAs based on published genome sequences of humans and other organisms such as the mouse. Such synthesis and assembly is known in the art and is practiced by commercial entities (e.g., DNA2.0, Menlo Park, Calif.; Blue Heron Biotechnology, Bothell, Wash.).

A benefit of the overall strategy to replace the endogenous Ig loci with components of the human Ig loci so as to produce human V domains optimized in vivo during primary and secondary immune responses is that the total number of loci altered is reduced compared to available strategies. The strategy of the present invention employs 2 or 3 altered loci, greatly simplifying the breeding process, and thereby providing an opportunity to introduce other useful mutations into the genetic background. Such useful mutations may include those that help break immune tolerance so as to more efficiently generate antibodies against human antigens that are very highly conserved between species. These include transgenic over-expression of CD19, knockout of the inhibitory receptor FcγRIIb, lpr or other autoimmune prone mutations, knockouts of the gene for the antigen, or zinc-finger transgenes engineered to silence expression of specific genes such as the antigen.

Another benefit of the overall strategy to replace the endogenous Ig loci with components of the human Ig loci is that it obviates trans recombination and trans switching that occurs between human Ig transgenes inserted in a chromosomal location outside the endogenous loci. The Ig chain product resulting from such trans recombination and trans switching events are chimeric for human-endogenous Ig sequences but deviate from the product design engineered in the transgene.

Yet another alternative is to incorporate fully human Ig loci including the human C regions, in place of the complete endogenous Ig loci and also replace the cluster of endogenous FcR genes with the orthologous cluster of human FcR genes using a similar BAC-based genetic engineering in homologous recombination competent cells, such as ES cells. In this way fully human antibodies can be produced, and during an immune response, these human antibodies can engage the human FcR normally. Such animals would also have the benefit of being useful for testing for the activity of effector function of human therapeutic mAb candidates in animal models of disease when bred onto the appropriate genetic background for the model, i.e., SCID, nu/nu, nod, and lpr mice. Further, the human target gene sequence can replace the endogenous gene using BAC targeting technology in homologous recombination-competent cells, such as ES cells, providing models for target validation and functional testing of the antibody.

Another embodiment incorporates fully human Ig including the human C regions comprising CH1-hinge-CH2-CH3 (-CH4) and the cognate syngeneic, e.g., mouse, membrane and intracellular domains so as to provide native intracellular signal transduction and to enable association of the IgH in the B-cell receptor with Igα and Igβ and therein allow murine-type signaling from the Igα, Igβ and IgG containing B-cell receptor. In yet another embodiment, the membrane and intracellular domain of the heavy chain constant region are from the same or non-cognate mouse heavy chain isotypes. Such engineering of the constant region genes can be readily accomplished using methods of the invention as detailed below.

Engineering the chimeric antibodies in this manner prevents the alteration in the V domain conformation resulting from the in vitro switch from a first C region, particularly a CH1 domain, and optionally a portion of the hinge region, from one species, e.g., mouse, with which it was evolved during the in vivo immune response to a second C region, particularly a CH1 domain, and optionally a portion of the hinge region, from another species, e.g., human. The antibodies produced by the knock-in animals of the present invention do not exhibit the reduction or loss of activity and potency seen in antibodies from other chimeric antibody producing animals when the human V region is appended to a human C region to make a fully human antibody, which may be caused by altered conformation of the VH domain resulting from the changing of the CH1 domain and/or by differences in antigen binding because of changed length or flexibility of the upper hinge regions (the peptide sequence from the end of the CH1 to the first cysteine residue in the hinge that forms an inter-heavy chain disulfide bond, and which are variable in length and composition) when switching from mouse to human constant region (Roux et al., J. Immunology (1997) 159:3372-3382 and references therein). The middle hinge region is bounded by the cysteine residues that form inter-heavy chain disulfide bonds.

Definitions

Before describing certain embodiments in detail, it is to be understood that this invention is not limited to particular compositions or biological systems, which can vary. It is also to be understood that the terminology used herein is for the purpose of describing particular illustrative embodiments only, and is not intended to be limiting. The terms used in this specification generally have their ordinary meaning in the art, within the context of this invention and in the specific context where each term is used. Certain terms are discussed below or elsewhere in the specification, to provide additional guidance to the practitioner in describing the compositions and methods of the invention and how to make and use them. The scope and meaning of any use of a term will be apparent from the specific context in which the term is used. As such, the definitions set forth herein are intended to provide illustrative guidance in ascertaining particular embodiments of the invention, without limitation to particular compositions or biological systems. As used in the present disclosure and claims, the singular forms "a," "an," and "the" include plural forms unless the context clearly dictates otherwise.

As used herein, "antibody" or "immunoglobulin" (Ig) refer to protein molecules produced by B cells that recognize and bind specific antigens and that may either be membrane bound or secreted. Antibodies may be monoclonal, in that they are produced by a single clone of B cells and therefore recognize the same epitope and have the same nucleic acid and amino acid sequence, or polyclonal, in that they are produced by multiple clones of B cells, recognize one or more epitopes of the same antigen and typically have different nucleic acid and amino acid sequences.

Antibody, or Ig, molecules are typically comprised of two identical heavy chains and two identical light chains linked together through disulfide bonds. Both heavy chains (IgH) and light chains (IgL) contain a variable (V) region or domain and a constant (C) region or domain. The portion of the IgH locus encoding the V region comprises multiple copies of variable (V), diversity (D), and joining (J) gene segments. The portion of the IgL loci, Igκ and Igλ, encoding the V region comprises multiple copies of V and J gene segments. The V region encoding portion of the IgH and IgL loci undergo gene rearrangement, e.g., different combinations of gene segments arrange to form the IgH and IgL variable regions, to develop diverse antigen specificity in antibodies. The secreted form of the IgH C region is made up of three C domains, CH1, CH2, CH3, optionally CH4 (Cμ), and a hinge region. The membrane-bound form of the IgH C region also has membrane and intra-cellular domains. The IgH constant region determines the isotype of the antibody, e.g. IgM, IgD, IgG1, IgG2, IgG3, IgG4, IgA and IgE. It will be appreciated that non-human mammals encoding multiple Ig isotypes will be able to undergo isotype class switching. There are two types of IgL, Igκ and Igλ.

A "Fab" domain or fragment comprises the N-terminal portion of the IgH, which includes the V region and the CH1 domain of the IgH, and the entire IgL. A "F(ab')$_2$" domain comprises the Fab domain and a portion of the hinge region, wherein the 2 IgH are linked together via disulfide linkage in the middle hinge region. Both the Fab and F(ab')$_2$ are "antigen-binding fragments." The C-terminal portion of the IgH, comprising the CH2 and CH3 domains, is the "Fc" domain. The Fc domain is the portion of the Ig recognized by cell receptors, such as the FcR, and to which the complement-activating protein, C1q, binds. The lower hinge region, which is encoded in the 5' portion of the CH2 exon, provides flexibility within the antibody for binding to FcR receptors.

As used herein "chimeric antibody" refers to an antibody translated from a polynucleotide sequence containing both human and non-human mammal polynucleotide sequences. A "humanized" antibody is one which is produced by a non-human cell or mammal and comprises human sequences, e.g., a chimeric antibody. Humanized antibodies are less immunogenic after administration to humans when compared to non-humanized antibodies prepared from another species. In addition, the humanized antibodies of the present invention can be isolated from a knock-in non-human mammal engineered to produce fully human antibody molecules. For example, a humanized antibody may comprise the human variable region of a chimeric antibody appended to a human constant region to produce a fully human antibody.

As used herein "chimeric Ig chain" refers to an Ig heavy chain or an Ig light chain translated from a polynucleotide sequence containing both human and non-human animal polynucleotide sequences. For example, a chimeric Ig heavy chain may comprise human VH, DH, JH, and CH1 gene segments and mouse CH2 and CH3 gene segments.

"Polypeptide," "peptide" or "protein" are used interchangeably to describe a chain of amino acids that are linked together by chemical bonds. A polypeptide or protein may be an IgH, IgL, V domain, C domain, or an antibody.

"Polynucleotide" refers to a chain of nucleic acids that are linked together by chemical bonds. Polynucleotides include, but are not limited to, DNA, cDNA, RNA, mRNA, and gene sequences and segments. Polynucleotides may be isolated from a living source such as a eukaryotic cell, prokaryotic cell or virus, or may be derived through in vitro manipulation by using standard techniques of molecular biology, or by DNA synthesis, or by a combination of a number of techniques.

"Locus" refers to a location on a chromosome that comprises one or more genes or exons, such as an IgH or Igκ locus, the cis regulatory elements, and the binding regions to which trans-acting factors bind. As used herein, "gene" or "gene segment" refers to the polynucleotide sequence encoding a specific polypeptide or portion thereof, such as a VL domain, a CH1 domain, an upper hinge region, or a portion thereof. As used herein, "gene segment" and "exon" may be used interchangeably and refer to the polynucleotide encoding a peptide, or a portion thereof. A gene, or gene segment, may further comprise one or more introns, transcriptional control elements, e.g., promoter, enhancers, or non-coding regions, e.g., cis regulatory elements, e.g., 5' and/or 3' untranslated regions, poly-adenylation sites.

The term "endogenous" refers to a polynucleotide sequence which occurs naturally within the cell or animal. "Orthologous" refers to a polynucleotide sequence that encodes the corresponding polypeptide in another species, i.e. a human CH1 domain and a mouse CH1 domain. The term "syngeneic" refers to a polynucleotide sequence that is found within the same species that may be introduced into an animal of that same species, i.e. a mouse Vκ gene segment introduced into a mouse Igκ locus.

As used herein, the term "homologous" or "homologous sequence" refers to a polynucleotide sequence that has a highly similar sequence, or high percent identity (e.g. 30%, 40%, 50%, 60%, 70%, 80%, 90% or more), to another polynucleotide sequence or segment thereof. For example, a DNA construct of the invention may comprise a sequence that is homologous to a portion of an endogenous DNA sequence to facilitate recombination at that specific location. Homologous recombination may take place in prokaryotic and eukaryotic cells.

As used herein, "flanking sequence" or "flanking DNA sequence" refers to a DNA sequence adjacent to the non-endogenous DNA sequence in a DNA construct that is homologous to an endogenous DNA sequence or a previously recombined non-endogenous sequence, or a portion thereof. DNA constructs of the invention may have one or more flanking sequences, e.g., a flanking sequence on the 3' and 5' end of the non-endogenous sequence or a flanking sequence on the 3' or the 5' end of the non-endogenous sequence.

The phrase "homologous recombination-competent cell" refers to a cell that is capable of homologously recombining DNA fragments that contain regions of overlapping homology. Examples of homologous recombination-competent cells include, but are not limited to, induced pluripotent stem cells, hematopoietic stem cells, bacteria, yeast, various cell lines and embryonic stem (ES) cells.

"Non-human mammal" refers to an animal other than humans which belongs to the class Mammalia. Examples of non-human mammals include, but are not limited to, non-human primates, rodents, bovines, ovines, equines, dogs, cats, goats, sheep, dolphins, bats, rabbits, and marsupials. Preferred non-human mammals rely primarily on gene conversion and/or somatic hypermutation to generate antibody diversity, e.g., mouse, rabbit, pig, sheep, goat, and cow. Particularly preferred non-human mammals are mice.

The term "knock-in" or "transgenic" refers to a cell or animal comprising a polynucleotide sequence, e.g., a transgene, derived from another species incorporated into its genome. For example, a mouse which contains a human VH gene segment integrated into its genome outside the endogenous mouse IgH locus is a transgenic mouse; a mouse which contains a human VH gene segment integrated into its genome replacing an endogenous mouse VH in the endogenous mouse IgH locus is a transgenic or a knock-in mouse. In knock-in cells and non-human mammals, the polynucleotide sequence derived from another species, may replace the corresponding, or orthologous, endogenous sequence originally found in the cell or non-human mammal.

A "humanized" animal, as used herein refers to a non-human animal, e.g., a mouse that has a composite genetic structure that retains gene sequences of the mouse or other non-human animal, in addition to one or more gene segments and or gene regulatory sequences of the original genetic makeup having been replaced with analogous human sequences.

As used herein, the term "vector" refers to a nucleic acid molecule into which another nucleic acid fragment can be integrated without loss of the vector's ability to replicate. Vectors may originate from a virus, a plasmid or the cell of a higher organism. Vectors are utilized to introduce foreign or recombinant DNA into a host cell, wherein the vector is replicated.

A polynucleotide agent can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and, where the polynucleotide encodes an RNA, for expressing the encoded RNA in a particular cell, either for subsequent translation of the RNA into a polypeptide or for subsequent trans regulatory activity by the RNA in the cell. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, alpha virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther.* 1:51-64, 1994; Flotte, *J. Bioenerg. Biomemb* 25:37-42, 1993; Kirshenbaum et al., *J. Clin. Invest* 92:381-387, 1993; each of which is incorporated herein by reference).

A DNA vector utilized in the methods of the invention can contain positive and negative selection markers. Positive and negative markers can be genes that when expressed confer drug resistance to cells expressing these genes. Suitable selection markers for *E. coli* can include, but are not limited to: Km (Kanamycin resistant gene), tetA (tetracycline resistant gene) and beta-lactamase (ampicillin resistant gene). Suitable selection markers for mammalian cells in culture can include, but are not limited to: hyg (hygromycin resistance gene), puro (puromycin resistance gene) and G418 (neomycin resistance gene). The selection markers also can be metabolic genes that can convert a substance into a toxic substance. For example, the gene thymidine kinase when expressed converts the drug gancyclovir into a toxic product. Thus, treatment of cells with gancylcovir can negatively select for genes that do not express thymidine kinase.

In a related aspect, the selection markers can be "screenable markers," such as green fluorescent protein (GFP), yellow fluorescent protein (YFP), red fluorescent protein (RFP), GFP-like proteins, and luciferase.

Various types of vectors are available in the art and include, but are not limited to, bacterial, viral, and yeast vectors. A DNA vector can be any suitable DNA vector, including a plasmid, cosmid, bacteriophage, p1-derived artificial chromosome (PAC), bacterial artificial chromosome (BAC), yeast artificial chromosome (YAC), or mammalian artificial chromosome (MAC). In certain embodiments, the DNA vector is a BAC. The various DNA vectors are selected as appropriate for the size of DNA inserted in the construct. In one embodiment, the DNA constructs are bacterial artificial chromosomes or fragments thereof.

The term "bacterial artificial chromosome" or "BAC" as used herein refers to a bacterial DNA vector. BACs, such as those derived from *E. coli*, may be utilized for introducing, deleting or replacing DNA sequences of non-human mammalian cells or animals via homologous recombination. *E. coli* can maintain complex genomic DNA as large as 350 kb in the form of BACs (see Shizuya and Kouros-Mehr, *Keio J Med.* 2001, 50(1):26-30), with greater DNA stability than cosmids or yeast artificial chromosomes. In addition, BAC libraries of human DNA genomic DNA have more complete and accurate representation of the human genome than libraries in cosmids or yeast artificial chromosomes. BACs are described in further detail in U.S. application Ser. No. 10/659,034 and 61/012,701, which are hereby incorporated by reference in their entireties.

DNA fragments comprising an Ig locus, or a portion thereof, to be incorporated into the non-human mammal are isolated from the same species of non-human mammal prior to humanization of the locus. Multiple BACs containing overlapping fragments of an Ig locus can be humanized and the overlapping fragments recombine to generate a continuous IgH or IgL locus. The resulting chimeric Ig locus comprises the human gene segments operably linked to the non-human mammal Ig gene segments to produce a functional Ig locus, wherein the locus is capable of undergoing gene rearrangement and thereby producing a diversified repertoire of chimeric antibodies.

These processes for recombining BACs and/or of engineering a chimeric Ig locus or fragment thereof requires that a bacterial cell, such as *E. coli*, be transformed with a BAC containing the host Ig locus or a portion thereof. The BAC containing bacillus is then transformed with a recombination vector comprising the desired human Ig gene segment linked to flanking homology sequence shared with the BAC containing the host Ig locus or portion thereof. The shared sequence homology mediates homologous recombination and cross-over between the human Ig gene segment on the recombination vector and the non-human mammal Ig gene segment on the BAC. Detection of homologously recombined BACs may utilize selectable and/or screenable markers incorporated into the vector. Humanized BACs can be readily isolated from the bacteria and used for producing knock-in non-human cells. Methods of recombining BACs and engineering insertions and deletions within DNA on BACs and methods for producing genetically modified mice therefrom are documented. See, e.g., Valenzuela et al. *Nature Biotech.* (2003) 21:652-659; Testa et al. *Nature Biotech.* (2003) 21:443-447; and Yang and Seed. *Nature Biotech.* (2003) 21:447-451.

The first recombination step may be carried out in a strain of *E. coli* that is deficient for sbcB, sbcC, recB, recC or recD activity and has a temperature sensitive mutation in recA.

After the recombination step, a recombined DNA construct is isolated, the construct having the various sequences and orientations as described.

The regions used for BAC recombineering should be a length that allows for homologous recombination. For example, the flanking regions may be from about 0.1 to 19 kb, and typically from about 1 kb to 15 kb, or about 2 kb to 10 kb.

The process for recombining BACs to make larger and/or tailored BACs comprising portions of the Ig loci requires that a bacterial cell, such as E. coli, be transformed with a BAC carrying a first Ig locus, a portion thereof, or some other target sequence. The BAC containing E. coli is then transformed with a recombination vector (e.g., plasmid or BAC) comprising the desired Ig gene segment to be introduced into the target DNA, e.g., one or more human VH, DH and/or JH gene segments to be joined to a region from the mouse IgH locus, both of which vectors have a region of sequence identity. This shared region of identity in the presence of functional recA in the E. coli mediates crossover between the Ig gene segment on the recombination vector and the non-human mammal Ig gene segment on the BAC. Selection and resolution of homologously recombined BACs may utilize selectable and/or screenable markers incorporated into the vectors. Humanized and chimeric human-mouse BACs can be readily purified from the E. coli and used for producing transgenic and knock-in non-human cells and animals by introducing the DNA by various methods known in the art and selecting and/or screening for either random or targeted integration events.

Alternatively, the DNA fragments containing an Ig locus to be incorporated into the non-human mammal are derived from DNA synthesized in vitro. The genomes of many organisms have been completely sequenced (e.g., human, chimpanzee, rhesus monkey, mouse, rat, dog, cat, chicken, guinea pig, rabbit, horse, cow) and are publicly available with annotation. In particular but not limited to, the human and mouse immunoglobulin loci have been studied and characterized for the location and activity of coding gene segments and non-coding regulatory elements. The sequences of the Ig loci may be manipulated and recombined in silico using commonly available software for nucleic acid sequence analysis. In silico recombination may be within the same locus, between two loci from the same species, or between two loci from two or more species. Sequences of an Ig locus may also be recombined in silico with those from a non-immunoglobulin locus, either from the same or a different species. Such sequences would include but are not limited to genes for positive and negative drug selection markers such as G418, hyg, puro and tk, and site-specific recombinase recognition sequences such lox P sites and its variants and frt sites. After assembling the desired sequence in silico, it may then be synthesized and assembled without errors (Kodumal et al., Proc. Natl. Acad. Sci. (2004) 101:15573-15578). The synthesis, assembly and sequencing of large DNAs are provided on a contractual basis (e.g., DNA 2.0, Menlo Park, Calif.; Blue Heron Biotechnology, Bothell, Wash.; and Eurogentec, San Diego, Calif.). Such synthetic DNA sequences are carried in vectors such as plasmids and BACs and can be transferred into other vectors such as YACs.

The term "construct" as used herein refers to a sequence of DNA artificially constructed by genetic engineering, recombineering or synthesis. In one embodiment, the DNA constructs are linearized prior to recombination. In another embodiment, the DNA constructs are not linearized prior to recombination.

As used herein, "loxP" and "CRE" refer to a site-specific recombination system derived from P1 bacteriophage. loxP sites are 34 nucleotides in length. When DNA is flanked on either side by a loxP site and exposed to CRE mediated recombination, the intervening DNA is deleted and the two loxP sites resolve to one. The use of the CRE/lox system, including variant-sequence lox sites, for genetic engineering in many species, including mice, is well documented. A similar system, employing frt sites and flp recombinase from S. cerevisiae can be employed to similar effect. As used herein, any implementation of CRE/loxP to mediate deletional events in mammalian cells in culture can also be mediated by the flp/frt system.

As used herein the term "immunize," "immunization," or "immunizing" refers to exposing the adaptive immune system of an animal to an antigen. The antigen can be introduced using various routes of administration, such as injection, inhalation or ingestion. Upon a second exposure to the same antigen, the adaptive immune response, i.e. T cell and B cell responses, is enhanced.

"Antigen" refers to a peptide, lipid or amino acid which is recognized by the adaptive immune system. Examples of antigens include, but are not limited to, bacterial cell wall components, pollen, and rh factor. "Target antigen" refers to an antigen, peptide, lipid, saccharide, or amino acid, which is recognized by the adaptive immune system which is chosen to produce an immune response against a specific infectious agent or endogenous cell. Target antigens include, but are not limited to, bacterial and viral components, tumor-specific antigens, cytokines, cell surface molecules, etc.

The term "pharmaceutical" or "pharmaceutical drug," as used herein refers to any pharmacological, therapeutic or active biological agent that may be administered to a subject or patient. In certain embodiments the subject is an animal, and preferably a mammal, most preferably a human.

The term "pharmaceutically acceptable carrier" refers generally to any material that may accompany the pharmaceutical drug and which does not cause an adverse reaction with the subject's immune system.

The term "administering," as used herein, refers to any mode of transferring, delivering, introducing, or transporting a pharmaceutical drug or other agent, such as a target antigen, to a subject. Such modes include oral administration, topical contact, intravenous, intraperitoneal, intramuscular, intranasal, or subcutaneous administration.

Knock-in Non-Human Mammals and Cells

Knock-in non-human mammals and cells of the present invention comprise altered IgH or IgL, or both, loci comprising orthologous human Ig gene segments, which replace the endogenous gene segments. For example, in specific embodiments a human CH1 domain which replaces a CH1 domain in a specific endogenous CH gene, e.g., Cμ, Cδ, Cγ, may be an orthologous sequence for each mouse CH region. For each of the endogenous Cγ genes, the replacing CH1 may be an orthologous human CH1 or may be a single Cγ from human CH genes from human IgG isotype more frequently used in therapeutic mAbs, typically Cγ1, Cγ2 or Cγ4, so as to better facilitate in vivo maturation of human V domain in the context of a more clinically relevant human CH1 domain.

Optionally, the upper hinge sequences of the endogenous C genes may also be replaced with the orthologous human C hinge sequences, respectively. Alternatively, the upper and middle hinge sequences of the endogenous C genes may also be replaced with the orthologous human C hinge sequences, respectively. If human middle hinge regions are used, the human Cγ4 middle hinge sequence may be engineered to contain a proline at residue at position 229 rather than a serine in order to drive inter-heavy chain dimerization via disulfide bonds. The lower hinge regions, part of the CH2 domain, of the endogenous Cγ genes would be left as is to facilitate optimal binding to endogenous FcγR. This engineering will produce human heavy chain Fab domain, Fab domain plus upper hinge, or F(ab')$_2$ if the upper and middle hinge regions are also converted to human, that will be more likely to retain optimal characteristics upon conversion to fully human IgG.

BACs comprising the endogenous IgH loci downstream of the J gene cluster and each retained C gene with the human CH1-endogenous CH2-CH3 (and CH4 for Cμ) and membrane and intracellular domain exons will be homologously recombined into the endogenous IgH locus in homologous recombination-competent cells, such as mouse ES cells, either as a first introduction step to be followed by replacement of the endogenous V-D-J genes with their human orthologs or in the opposite order, introduction of human V, D and J followed by endogenous C genes engineered as described above. The content on the Ig locus on the BAC is not restricted to only C gene segments on one and V, D and J gene segments on the other. The BAC with the C gene segments may also contain J gene segments and even D gene segments and even one or more V gene segments. Alternatively, the BAC with V gene segments may contain D gene segments and even J gene segments and even one or more C gene segments.

BACs carrying the constant region genes may be engineered in E. coli or synthesized in vitro prior to introduction into ES cells so as to delete any unwanted gene segments, such as the Cε and Cα genes. This would constrain the knock-in animals to make Cμ and Cδ for primary immune responses and Cγ isotypes for secondary, affinity-matured immune responses, from which therapeutic antibody candidates would typically be recovered. The endogenous IgH 3' LCR may be left unaltered.

A similar replacement strategy would be employed for the endogenous Igκ locus except that the complete human Cκ gene could optionally also be incorporated in the BAC so as to replace the endogenous Cκ locus, thus producing fully human Igκ chains. The human Cλ locus could also be incorporated in a similar manner.

Yet another aspect of the invention comprises incorporating fully human Ig loci including the human C regions, in place of the complete endogenous Ig loci. In this embodiment, the cluster of endogenous FcR genes is also replaced with the orthologous cluster of human FcR genes using similar BAC-based genetic engineering in homologous recombination competent cells, such as mouse ES cells. The cluster of endogenous FcγR genes can be replaced in the same ES cell in which the human IgH locus or portions thereof have replaced the endogenous locus or in a separate ES cell. In the latter instance, mice would be derived from said ES cells and bred with mice carrying the engineered Ig locus (loci) so as to produce mice that make human IgG antibodies that bind to human FcγR in place of mouse FcγR genes. In either way fully human antibodies would be produced and during an immune response would be able to engage the human FcR receptors normally. Such knock-in animals would also have the benefit of being useful for testing for the activity and effector function of human therapeutic mAb candidates in models of disease when bred onto the appropriate genetic background for the model, i.e., SCID, nu/nu, nod, and lpr mice. Further, the human target gene sequence can replace the endogenous gene using BAC targeting technology in homologous recombination-competent cells, providing models for target validation and functional testing of the antibody. In this instance, the human CH genes may be engineered to have cytoplasmic and/or membrane domain gene segments from mouse or other orthologous species to facilitate native signal transduction in the B cell.

In addition, another aspect of the invention relates to the design of the desired human V region. In particular, an entire human V domain repertoire or a portion thereof may be incorporated into the genome of the cell, or a tailored V domain repertoire may be incorporated. For example, in certain embodiments it is preferred to omit V domain gene segments that are missing from some human haplotypes and instead tailoring the V domain repertoire to be composed of only the functional V gene segments common across all known human haplotypes. Doing so provides antibody drug candidates with V domains that are better immune tolerized across all potential patients, thereby preventing the induction of a dangerous immune response upon administration of the encoded antibody to a subject. One or more V domain gene segments may be incorporated.

In preferred embodiments of the invention, BACs containing the desired Ig loci gene segments are used to incorporate this genetic information into the target cell via homologous recombination. The nature of BAC engineering in E. coli provides additional opportunities to finely tailor the immunoglobulin loci prior to introduction into competent cells. For example, the human DH cluster can be replaced or supplemented with D genes from other species, such as from non-human primates, rabbits, rat, hamster etc. BAC libraries and the complete sequence of the Ig loci are available for many species. D gene segments within the IgH loci can be defined from publicly available sequence or genetic structure information, or by testing using appropriate D specific probes or primers. The orthologous D gene clusters or portions thereof can be homologously recombined into the BACs or assembled in silico and then synthesized, therein replacing or adding to the cluster of human D gene segments. Because of the significant diversification that occurs in making the complementarity determining region-3 (CDR3) and because the structure of the V region is such that the CDR3 is usually solvent inaccessible, immunogenicity to the CDR3 sequence is of less concern. Therefore, amino acids encoded by non-human D genes incorporated into the CDR3 are less likely to be immunogenic. Non-human D genes could confer an advantage by producing novel CDR3 structures that would expand the range of epitope specificities and affinities in a panel of antigen-specific antibodies, therein broadening the quality of activities mediated by a panel of mAbs.

Similarly, the JH gene cluster, i.e., one or more JH gene segments, can be from a species other than human due to the relative sequence conservation across mammals. The JH gene segment may be derived from any mammal, e.g., human, non-human primate, rabbit, sheep, rat, hamster, and mouse. In particular embodiments, the JH gene segment is human.

After engineering the Ig loci into homologous recombination-competent cells to replace portions or all of the endogenous Ig loci, genetically engineered non-human mammals, such as mice, can be produced by now-standard methods such as blastocyst microinjection followed by breeding of chimeric animals, morula aggregation or cloning methodologies, such as somatic cell nuclear transfer. For example, mice with modified IgH and IgL loci can be bred to produce homozygous IgH and IgL (either Igκ or Igλ).

Multi-stage breeding would produce animals homozygous for modified IgH, Igκ and Igλ loci. Animals heterozygous for IgH and IgL loci, which would produce both fully-mouse and human-mouse antibodies, can also be used to generate antigen-specific human V-mouse C mAbs, though somewhat less efficiently than using homozygous animals because there would also be production of antibody from the active endogenous Ig loci. Mice heterozygous and homozygous for just one altered locus, e.g, IgH, could also be useful as a source of human VH domains (VH-CH1) for antibody display libraries and when mixed with VL domains from mice heterozygous or homozygous for an altered IgL locus, especially if the mice were immunized (see below). For example, an antibody display library from two separate mice—one with human VH-CH1-mouse CH2-CH3 and the other with human VK-CK—could be used to recover fully human antibodies using well-established techniques in molecular biology. Mice heterozygous and homozygous for more than one altered locus, e.g., IgH and Igκ, would also be useful as a source of human VH and VL domains for antibody display libraries.

Certain embodiments provide a method of producing a knock-in non-human mammal having a genome encoding human VH and CH1 gene segments and a human Ig light chain locus comprising the steps of breeding a non-human mammal comprising a chimeric Ig heavy chain locus, wherein the Ig heavy chain locus comprises the human VH and CH1 gene segments, with a non-human mammal comprising a human Ig light chain locus; selecting offspring having a genome comprising the chimeric Ig heavy chain locus and the human Ig light chain locus; further breeding the offspring; and producing offspring having a genome homozygous for the chimeric heavy and human light chain loci. In related embodiments, the genome of the mammal also encodes a human JH gene segment.

This genetic engineering strategy can also be applied to engineering of animals other than mice so as to express human sequence V regions coupled with xenogeneic C regions, or completely human antibodies, or some intermediate thereof. For animals for which there is a current lack of ES cell technology for genetic engineering through blastocyst microinjection or morula aggregation, the endogenous loci can be modified in cells amenable to various cloning technologies or developmental reprogramming (e.g., induced pluripotent stem cells, IPS). The increased frequency of homologous recombination provided by the BAC technology provides the ability to find doubly replaced loci in the cells, and cloned animals derived therefrom would be homozygous for the mutation, therein saving time and costs especially when breeding large animals with long generation times. Iterative replacements in the cultured cells could provide all the requisite engineering at multiple loci and then direct production of animals using cloning or IPS technology, without cross-breeding to get the appropriate genotypes. The ability to finely tailor the introduced Ig genes and also finely specify the sites into which they are introduced provides the ability to engineer enhancements that would provide better function. Engineered animals such as goats, bovines, ovines, equines, rabbits, dogs etc. would be a source of fully human polyclonal antibodies.

Furthermore, if the BACs were engineered in *E. coli* with the DNA components required for chromosome function, e.g., telomeres and a centromere, preferably, but not required, of the recipient species for optimal function, e.g., mouse telomeres and a mouse centromere, they can be introduced into the recipient cell by electroporation, microinjection etc. and would function as artificial chromosomes.

These BAC-based artificial chromosomes also could be used as a foundation for subsequent rounds of homologous recombination for building up larger artificial chromosomes.

The engineered Ig locus or loci described herein on vectors such as plasmids, BACs or YACs can also be used as standard transgenes introduced via microinjection into the pronucleus of an embryo such as mouse, rabbit, rat, or hamster. Several BACs, YACs, plasmids or any combination thereof can be co-microinjected and will co-integrate to make a functional locus. Various methods known in the art can be used to inactivate the endogenous Ig loci and the animals with an engineered Ig transgene bred with those with one or more inactivated endogenous loci to derive genotypes expressing antibodies from the transgene and without production of the complete native immunoglobulin from the inactivated endogenous loci.

Antibodies

Animals carrying the modified loci can be immunized with target antigens using various techniques in the art. Target antigens may be selected for the treatment or prevention of a particular disease or disorder, such as various types of cancer, graft versus host disease, cardiovascular disease and associated disorders, neurological diseases and disorders, autoimmune and inflammatory disorders, and pathogenic infections. In other embodiments, target antigens may be selected to develop an antibody that would be useful as a diagnostic agent for the detection one of the above diseases or disorders.

Antigen-specific repertoires can be recovered from immunized mice by hybridoma technology, single-cell RT-PCR for selected B cells, by antibody display technologies, and other methods known in the art. For example, to recover mAbs from mouse-derived hybridomas, a human V-CH1-mouse hinge+CH2+CH3 antibody or a human V-CH1-upper/middle hinge-mouse lower hinge+CH2+CH3 antibody (depending upon the IgH locus engineering) would be secreted into the culture supernatant and can be purified by means known in the art such as column chromatography using protein A, protein G, etc. Such purified antibody can be used for further testing and characterization of the antibody to determine potency in vitro and in vivo, affinity etc.

In addition, since they can be detected with anti-mouse constant region secondary agents, the human V-CH1 (upper/middle hinge)-mouse CH2-CH3 mAb may be useful for immunochemistry assays of human tissues to assess tissue distribution and expression of the target antigen. This feature of the chimeric antibodies of the present invention allows for specificity confirmation of the mAb over fully human mAbs because of occasional challenges in using anti-human constant region secondary detecting agents against tissues that contain normal human Ig and from the binding of human Fc regions to human FcR expressed on cells in some tissues.

The human variable regions of the mAbs can be recovered and sequenced by standard methods. Either before or after identifying lead candidate mAbs, the genes, either genomic DNA or cDNAs, for the human VH and VL domains can be recovered by various molecular biology methods, such as RT-PCR, and then appended to DNA encoding the remaining portion of the human constant region, therein producing fully human mAb. The DNAs encoding the now fully human VH-CH and human VL-CL would be cloned into suitable expression vectors known in the art or that can be custom-built and transfected into mammalian cells, yeast cells such as Pichia, other fungi etc. to secrete antibody into the culture supernatant. Other methods of production such as ascites using hybridoma cells in mice, transgenic animals that secrete the antibody into milk or eggs, and transgenic plants that make antibody in the fruit, roots or leaves can also be used for expression. The fully human recombinant antibody can be purified by various methods such as column chromatography using protein A, protein G etc.

The purified antibody can be lyophilized for storage or formulated into various solutions known in the art for solubility and stability and consistent with safe administration into animals, including humans. Purified recombinant antibody can be used for further characterization using in vitro assays for efficacy, affinity, specificity, etc., animal models for efficacy, toxicology and pharmacokinetics etc. Further, purified antibody can be administered to humans for clinical purposes such as therapies and diagnostics for disease.

Various fragments of the human V-CH1-(upper/middle hinge)-endogenous CH2-CH3 mAbs can be isolated by methods including enzymatic cleavage, recombinant technologies, etc. for various purposes including reagents, diagnostics and therapeutics. The cDNA for the human variable domains+CH1 or just the human variable domains can be isolated from the engineered non-human mammals described above, specifically from RNA from secondary lymphoid organs such as spleen and lymph nodes, and the VH and VL cDNAs implemented into various antibody display systems such as phage, ribosome, E. coli, yeast, mammalian etc. The knock-in mammals may be immunologically naïve or optimally may be immunized against an antigen of choice. By using appropriate PCR primers, such as 5' in the leader region or framework 1 of the variable domain and 3' in the human CH1 of Cγ genes, the somatically matured V regions can be recovered in order to display solely the affinity matured repertoire. The displayed antibodies can be selected against the target antigen to efficiently recover high-affinity antigen-specific fully human Fv or Fabs, and rid of the knock-in mammal of CH2-CH3 domains that would be present if mAbs were recovered directly from the knock-in mammals.

Methods of Use

Purified antibodies of the present invention may be administered to a subject for the treatment or prevention of a particular disease or disorder, such as various types of cancer, graft versus host disease, cardiovascular disease and associated disorders, neurological diseases and disorders, autoimmune and inflammatory disorders, allergies, and pathogenic infections. In preferred embodiments, the subject is human.

Antibody compositions are administered to subjects at concentrations from about 0.1 to 100 mg/ml, preferably from about 1 to 10 mg/ml. An antibody composition may be administered topically, intranasally, or via injection, e.g., intravenous, intraperitoneal, intramuscular, intraocular, or subcutaneous. A preferred mode of administration is injection. The administration may occur in a single injection or an infusion over time, i.e., about 10 minutes to 24 hours, preferably 30 minutes to about 6 hours. An effective dosage may be administered one time or by a series of injections. Repeat dosages may be administered twice a day, once a day, once a week, bi-weekly, tri-weekly, once a month, or once every three months, depending on the pharmacokinetics, pharmacodynamics and clinical indications. Therapy may be continued for extended periods of time, even in the absence of any symptoms.

A purified antibody composition may comprise polyclonal or monoclonal antibodies. An antibody composition may contain antibodies of multiple isotypes or antibodies of a single isotype. An antibody composition may contain unmodified chimeric antibodies, or the antibodies may have been modified in some way, e.g., chemically or enzymatically. An antibody composition may contain unmodified human antibodies, or the human antibodies may have been modified in some way, e.g., chemically or enzymatically. Thus an antibody composition may contain intact Ig molecules or fragments thereof, i.e., Fab, F(ab')$_2$, or Fc domains.

Administration of an antibody composition against an infectious agent, alone or in combination with another therapeutic agent, results in the elimination of the infectious agent from the subject. The administration of an antibody composition reduces the number of infectious organisms present in the subject 10 to 100 fold and preferably 1,000 fold, and more than 1,000 fold.

Similarly, administration of an antibody composition against cancer cells, alone or in combination with another chemotherapeutic agent, results in the elimination of cancer cells from the subject. The administration of an antibody composition reduces the number of cancer cells present in the subject 10 to 100 fold and preferably 1,000 fold, and more than 1,000 fold.

In certain aspects of the invention, an antibody may also be utilized to bind and neutralize antigenic molecules, either soluble or cell surface bound. Such neutralization may enhance clearance of the antigenic molecule from circulation. Target antigenic molecules for neutralization include, but are not limited to, toxins, endocrine molecules, cytokines, chemokines, complement proteins, bacteria, viruses, fungi, and parasites. Such an antibody may be administered alone or in combination with other therapeutic agents including other antibodies, other biological drugs, or chemical agents.

It is also contemplated that an antibody of the present invention may be used to enhance or inhibit cell surface receptor signaling. An antibody specific for a cell surface receptor may be utilized as a therapeutic agent or a research tool. Examples of cell surface receptors include, but are not limited to, immune cell receptors, adenosine receptors, adrenergic receptors, angiotensin receptors, dopamine and serotonin receptors, chemokine receptors, cytokine receptors, histamine receptors, etc. Such an antibody may be administered alone or in combination with other therapeutic agents including other antibodies, other biological drugs, or chemical agents.

It is also contemplated that an antibody of the present invention may be further modified to enhance therapeutic potential. Modifications may include direct- and/or indirect-conjugation to chemicals such as chemotherapeutic agents, radioisotopes, siRNAs, double-stranded RNAs, etc. Other modifications may include Fc regions engineered for either increased or decreased antibody-dependent cellular cytotoxicity, either increased or decreased complement-dependent cytotoxicity, or increased or decreased circulating half-life.

In other embodiments, an antibody may be used as a diagnostic agent for the detection one of the above diseases or disorders. A chimeric antibody may be detected using a secondary detection agent that recognizes a portion of the antibody, such as an Fc or Fab domain. In the case of the constant region, the portion recognized may be a CH1, CH2, or a CH3 domain. The Cκ and Cλ domain may also be recognized for detection. Immunohistochemical assays, such as evaluating tissue distribution of the target antigen, may take advantage of the chimeric nature of an antibody of the present invention. For example, when evaluating a human tissue sample, the secondary detection agent reagent recognizes the non-human portion of the Ig molecule, thereby reducing background or non-specific binding to human Ig molecules which may be present in the tissue sample.

Pharmaceutical Compositions and Kits

The present invention further relates to pharmaceutical compositions and methods of use. The pharmaceutical compositions of the present invention include an antibody, or fragment thereof, in a pharmaceutically acceptable carrier. Pharmaceutical compositions may be administered in vivo for the treatment or prevention of a disease or disorder. Furthermore, pharmaceutical compositions comprising an antibody, or a fragment thereof, of the present invention may include one or more agents for use in combination, or may be administered in conjunction with one or more agents.

The present invention also provides kits relating to any of the antibodies, or fragment thereof, and/or methods described herein. Kits of the present invention may include diagnostic or treatment methods. A kit of the present invention may further provide instructions for use of a composition or antibody and packaging.

A kit of the present invention may include devices, reagents, containers or other components. Furthermore, a kit of the present invention may also require the use of an apparatus, instrument or device, including a computer.

EXAMPLES

The following examples are provided as further illustrations and not limitations of the present invention. The teachings of all references, patents and published applications cited throughout this application, as well as the Figures are hereby incorporated by reference.

Example 1

Design of BACs in E. Coli

As described in US Patent Application Publication No. 2004/0128703, the manipulation of BACs in E. coli provides a powerful tool for fine tailoring of the genomic DNA carried in the BACs. For example, to replace mouse CH1 with human CH1 in one or more of the mouse constant region genes, e.g., Cγ1 or all mouse Cγ genes or mouse Cμ, Cδ and all the mouse Cγ genes, a modified mouse BAC is made in E. coli and then used for homologous recombination in ES cells. For example, in the targeting BAC, the mouse CH1 exons of at least one and up to all of the Cγ genes are replaced by the human CH1 exons. This replacement is similarly performed in E. coli using a homologous recombination method. The resulting modified BAC has a germline-configured segment carrying the human D region, the human J region, and downstream mouse Cμ region, Cδ region, Cγ3 region (mouse CH1 of γ3 is replaced by human CH1), modified Cγ1 region (mouse CH1 of γ1 is replaced by human CH1), modified Cγ2B region (mouse CH1 of γ2B is replaced by human CH1), and modified Cγ2C (mouse CH1 of γ2C is replaced by human CH1). This strategy can also be used to modify the CH1 exons of Cμ and Cδ genes. Other precise replacements such as the upper and middle hinge region coding sequence with human for mouse can also be made. Further finely tailored changes including as small as single codon and single nucleotide changes can be engineered into the replacing DNA.

Example 2

Homologous Recombination of BACs in E. Coli

A BAC vector is based on the F-factor found in E. coli. The F-factor and the BAC vector derived from it are maintained as low copy plasmids, generally found as one or two copies per cell depending upon its life cycle. Both F-factor and BAC vector show the fi$^+$ phenotype, which excludes an additional copy of the plasmid in the cell. By this mechanism, when E. coli already carries and maintains one BAC, and then an additional BAC is introduced into the E. coli, the cell maintains only one BAC, either the BAC previously existing in the cell or the external BAC newly introduced. This feature is extremely useful for selectively isolating BACs homologously recombined as described below.

The homologous recombination in E. coli requires the functional RecA gene product. In this example, the RecA gene has a temperature-sensitive mutation so that the RecA protein is only functional when the incubation temperature is below 37° C. When the incubation temperature is above 37° C., the Rec A protein is non-functional or has greatly reduced recombination activity. This temperature sensitive recombination allows manipulation of RecA function in E. coli so as to activate conditional homologous recombination only when it is desired. It is also possible to obtain, select or engineer cold-sensitive mutations of Rec A protein such that the protein is only functional above a certain temperature, e.g., 37° C. In that condition, the E. coli would be grown at a lower temperature, albeit with a slower generation time, and recombination would be triggered by incubating at above 37° C. for a short period of time to allow only a short interval of recombination.

Homologous recombination in E. coli is carried out by providing overlapping DNA substrates that are found in two circular BACs. The first BAC (BAC1) carries the contiguous segments from A through E, and the second BAC (BAC2) carries the contiguous segments from E through I. The segment E carried by both BACs is the overlapping segment where the DNA crossover occurs, and as a result it produces a recombinant that carries the contiguous segments from A through I.

BAC1 described above is the one already present in the cell, and when BAC2 is introduced into the cell, either BAC1 or BAC2 can exist in the cell, not both BACs. Upon electroporation of BAC2 into the cell, the temperature would be lowered below 37° C. so as to permit conditional RecA activity, therein mediating homologous recombination. If BAC1 and BAC2 have a selectable marker each and the markers are distinctively different, for example, BAC1 carries Kan (a gene conferring kanamycin resistance) and BAC2 carries Amp (a gene giving Ampicilin resistance), only the recombinant BAC grows in the presence of both antibiotics Kan and Amp.

Since there are two E gene segments at the separate region of the recombinant BAC, the E segment flanked by two vectors must be removed by one of two ways, one is by homologous recombination at either the vectors or the E region, and the other is carried out by loxP site specific recombination by CRE recombinase. The resolved BAC has now the contiguous stretch from A through I with single copy of E.

Example 3

Homologous Recombination in E. Coli

According to the procedure detailed above, BAC1 and BAC2 undergo recombination in E. coli. BAC1 and BAC2 have 156,427 bp and 122,500 bp, respectively, and they overlap by 42,363 bp. The size of the resulting BAC after recombination and resolution is 236,564 bp. BAC2 containing an Amp gene in the BAC vector or in the appropriate area of the BAC is introduced into an *E. coli* bacillus carrying BAC1 having a Kan gene in the BAC vector or in the appropriate area of the BAC.

The introduction of a BAC to *E. coli* cell is typically done by electroporation. Prior to electroporation, the cells are maintained at 40° C., a non-permissive temperature for recombination, and after electroporation the cells are incubated at 30° C., a temperature permissive for recombination. During the incubation, homologous recombination occurs and cells express enzymes necessary to become resistant to both antibiotics. The incubation period is about 45 to 90 minutes. Then the cells are spread on the media plates containing both antibiotics and the plates are incubated at 40° C. to prevent further homologous recombination. The majority of colony isolates growing on the media plates have the recombined BAC that has predicted size. This can be confirmed by pulsed field gel electrophoresis analysis. Integrity of the recombined DNA is confirmed with restriction digests using rare-cutting and infrequent cutting restriction enzyme digests analyzed by pulsed field gel electrophoresis.

Example 4

Design of a BAC to Replace Endogenous CH1 with Human CH1

In this example, two BACs (173, 869 bp and 102,413 bp) overlap by 6,116 bp recombine to produce a 270,165 bp BAC. To replace mouse CH1 in the mouse BAC with human CH1, an appropriate DNA construct is made. The construct is made by chemical synthesis, PCR, conventional cloning techniques or a combination of these methods. The construct has a human CH1 sequence flanked by mouse sequence arms that, in the mouse genome, flank the mouse CH1 region as well.

The construct is recombined in *E. coli* with the original mouse BAC at one or the other side of the homologous flanking mouse DNA sequences, and after repeated recombination and resolution by Cre recombinase, a chimeric BAC having human CH1 replacing mouse CH1 is made. By repeating this process, all of the mouse CH1 regions of the Cγ genes are replaced with human CH1 regions, producing a modified BAC carrying all of the Cγ genes having human CH1 in place of the mouse CH1.

Similarly, the mouse CH1 domains of Cμ, Cδ can be replaced by the corresponding human CH1 domains. If desired, Cα and Cε can also be modified in this manner. Similar replacement(s) can also be performed with the upper and/or middle hinge segments of the C gene(s). If incorporating a human middle hinge region, the human Cγ4 middle hinge encoding DNA sequence can be engineered, such as by chemical synthesis, with a codon encoding proline replacing the codon encoding serine 229 to effect interchain rather than intrachain disulfide bind formation to stabilize the IgG4 dimer.

Example 5

Introduction of BACs into Cells

In preparation for introduction into ES cells, mammalian expression cassettes for selectable markers and for screenable markers can be recombined onto the BACs. Such cassettes carry genes with required regulatory elements such as promoters, enhancers and poly-adenylation sites for expression of the genes in mammalian cells, such as mouse ES cells. The genes on the cassette can be selectable markers such as drug-resistance and drug-sensitivity genes for drugs such as G418, hygromycin, puromycin, gancyclovir (thymidine kinase), hypoxanthine phosphoribosyl transferase etc. and screenable markers such as green-fluorescent protein (GFP), red-fluorescent protein (RFP), luciferase etc. Such markers are used to select and screen for cells into which the BAC has been introduced and homologously recombined.

For introduction into ES cells, BAC DNA is purified from *E. coli* and the *E. coli* genomic DNA by methods known in the art such as the alkaline lysis method, commercial DNA purification kits, CsCl density gradient, sucrose gradient, or agarose gel electrophoresis, which may be followed by treatment with agarase. To linearize the purified DNA, it is then digested by NotI. The two NotI sites flank the cloning site on the BAC vector and thus NotI digestion separates the insert from the vector. The insert DNA is free from the vector DNA, which has a loxP site, except the small region between the cloning site and NotI site. Thus, the DNA to be transfected into the mammalian cell does not carry a loxP site unless one is purposely engineered into the DNA to be transfected into the mammalian cell. Although NotI site is extremely rare on human and mouse immunoglobulin genomic DNA, if the BAC DNA construct contains one or more NotI sites, sites for other rare restriction enzymes such as AscI, AsiSI, FseI, PacI, PmeI, SbfI, and SwaI, homing endonucleases such as I-CeuI, I-SceI, PI-PspI, PI-SceI, or lambda terminase will be introduced into the junction area between the insert and the vector. This can be accomplished by transposon, homologous recombination, and other cloning methods. The linearized DNA, typically 0.1-10 μg of DNA depending upon the size, are introduced into the mammalian cells, such as ES cells, by methods known in the art such as transfection, lipofection, electroporation, Ca-precipitation or direct nuclear microinjection.

Example 6

Engineering of Ig Loci Via Incorporation of Large BACs Via Sequential Replacement in Embryonic Stem Cells Homologous recombination in *E. coli* to construct larger BACs is described in U.S. Patent Application Publication No. 2004/0128703. Such methods can be used to make BACs with larger inserts of DNA than is represented by the average size of inserts of currently available BAC libraries. Such larger inserts can comprise DNA representing the human Ig loci such IgH, Igκ and Igλ. The DNA inserts can also comprise DNA representing the endogenous Ig loci including some or all of the DNA representing the constant region genes, which also may carry modifications designed into the DNA.

Figure 1B:
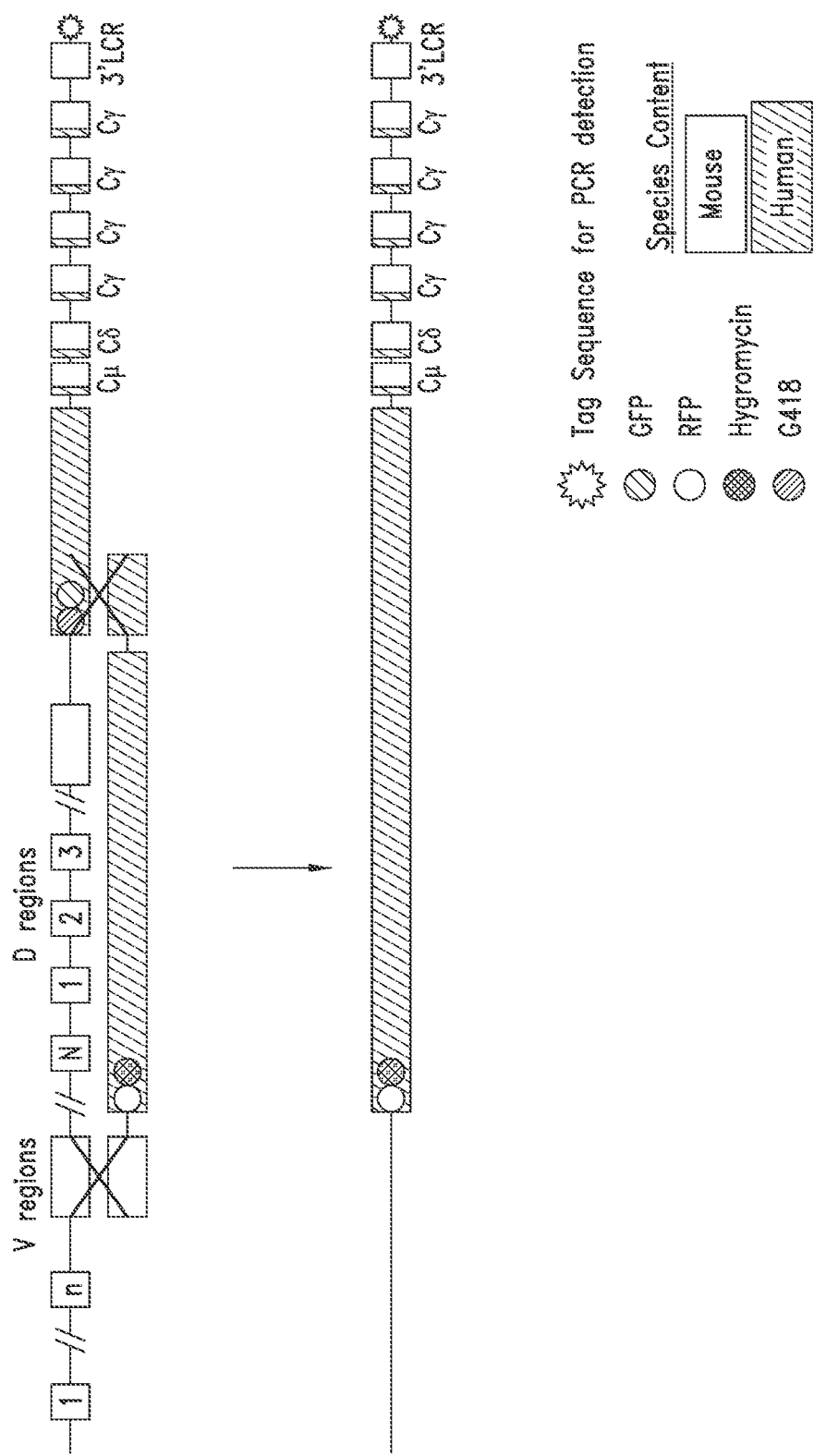
Figure 1C:
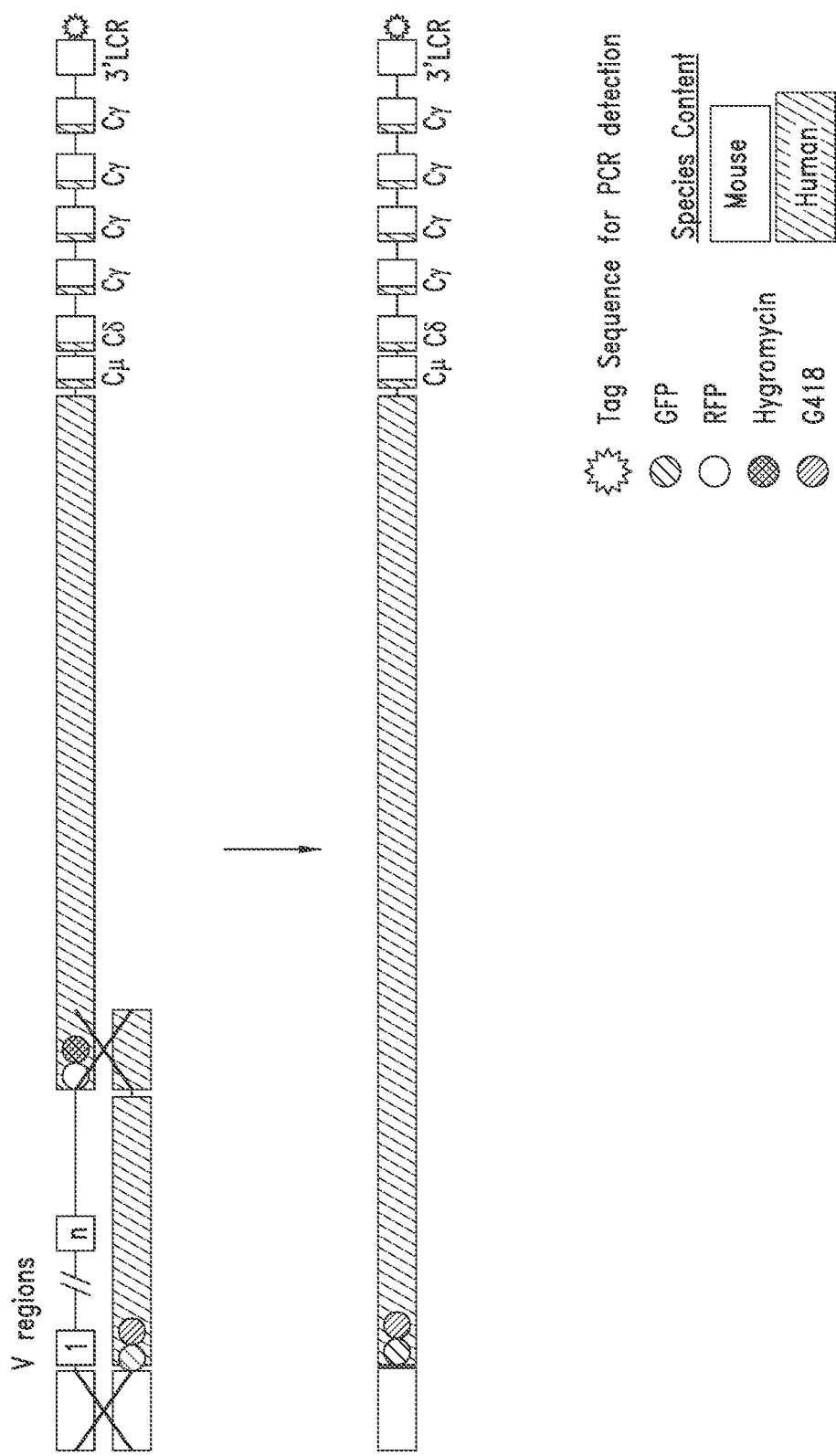

As an example, using such longer BACs, the region containing the human IgH V, D and J gene segments is covered by only 3 to 4 separate BACs, each of which would be approximately ~300 kb in size (FIG. 1). The region containing the mouse IgH constant region gene segments from downstream of the JH gene segment cluster through just upstream of the mouse 3' locus control region can be covered in a single BAC of 170-180 kb. These BACs also carry overlapping segments to provide homology with the subsequent BAC for homologous recombination in cells such as ES cells. Using these longer BACs, the V, D and J gene segments of the mouse IgH are sequentially replaced with the corresponding human sequences and the constant region gene segments of the mouse IgH are replaced with engineered human-mouse constant region gene segments. The sequential replacements are substantially complete to the desired amount.

The first BAC to be introduced into ES cells may be comprised of human Ig DNA flanked on either side by 1 kb to 10 kb to 100 kb or more of mouse DNA from the corresponding endogenous mouse genome in the ES cell. The first BAC then replaces a portion of the endogenous mouse genome by homologous recombination in ES cells, replacing the endogenous mouse DNA between the two flanking DNAs, which are the targeting sites, with the human DNA engineered between the flanking DNAs on the BAC. For example, by constructing in E. coli a BAC that contains a known size in kilobases of human IgH DNA that contains human variable regions, the DH gene cluster and the JH cluster, flanked on the 3' end by mouse DNA corresponding to the region 3' of the mouse JH locus and flanked 5' by mouse DNA corresponding to the region the same known size in kilobases 5' of the mouse JH cluster, and introducing the purified BAC into mouse ES cells to allow for homologous recombination, the corresponding mouse VH, DH and JH genes would be replaced by the orthologous human DNA.

The flanking mouse DNAs could also be further away, e.g., the 5' homology could be upstream of the most 5' endogenous VH gene so that upon homologous recombination, the entire mouse VH-DH-JH region would be replaced by the human VH-DH-JH on the BAC. In other words, the length of the region of the endogenous DNA to be replaced is determined by the distance between the two flanking mouse segments on the BAC. The distance is not the actual length between the flanking mouse segments in the BAC; rather it is the distance between the flanking mouse segments in the endogenous mouse chromosome. This distance may be calculated from the available genomic databases, such as UCSC Genomic Bioinformatics, NCBI and others known in the art.

A second, and any subsequent, BAC would have two segments flanking the DNA to be introduced. For the two flanking DNAs, one is comprised of human DNA that corresponds to all or a portion of the human DNA introduced into the cell genome in the first replacement and the other is mouse DNA corresponding to endogenous DNA upstream (or downstream as the case may be) of the region to be replaced in the second introduction.

Upon introduction into a homologous recombination-competent cell such as a mouse ES cell into which a first BAC DNA has replaced a portion of the endogenous locus, e.g., into the mouse IgH locus, one crossover would occur between the human flanking sequence of the BAC and the human sequence in the modified mouse chromosome, and the other between the mouse sequence of the BAC and the corresponding mouse region of said chromosome (see FIG. 1B and FIG. 10). Put another way, in the second BAC, the human flanking sequence includes a homologous segment to the end portion of the human DNA sequence of the first BAC previously integrated into the chromosome.

In this way, when they are joined by homologous recombination in ES cells, the joined segments become a contiguous segment. Such a segment may be germline-configured as it is naturally found in humans or because of purposely engineered insertions, deletions or rearrangements may have a configuration different from germline. The mouse flanking sequence in the second BAC corresponds to the mouse endogenous chromosomal DNA that is a specified, desired distance away from the newly introduced human sequence in the mouse chromosome. The distance between the two mouse segments are long enough so that the replacement of the mouse endogenous IgH is completed as planned after repeated homologous recombination.

For instance, using BACs with suitable human DNA inserts of the VH, DH, and JH loci and flanked with suitably located targeting DNAs, it would be possible to replace all of the endogenous mouse VH, DH and JH genes with their corresponding human counterparts with 2-3 sequential replacements with BACs suitably engineered in E. coli as outlined above to facilitate homologous recombination in mammalian cells, including ES cells, and therein leaving the human V-D-J genes operably linked to downstream mouse constant region loci. In a third, fourth or fifth replacement, using a BAC with a suitable human DNA insert carrying human Cµ, Cδ and Cγ genes and optionally Cα, Cε and the human 3' locus control region (LCR), and flanked by human and mouse DNAs corresponding to introduced and endogenous DNA, respectively, the endogenous mouse C regions can be replaced with their human counterparts.

Alternatively, the genomic DNA comprising the constant region genes may be of mouse origin and may be engineered with desired modifications such as replacing the CH1 domain of all or selected mouse constant regions with human CH1 DNA, and/or upper and the optional middle hinge regions of some or all of the mouse C genes with corresponding human gene sequences, all flanked by appropriate targeting DNA as outlined above. Further, some of the mouse C regions, e.g., Cε and/or Cα and/or one and up to all of the Cγ gene segments, can be deleted such that the endogenous mouse 3' LCR would be in closer than germline proximity to the most 3' constant region on the BAC, and upon homologous recombination into the genome, effecting deletion of the endogenous C gene segments absent from the targeting BAC.

The order of introduction of the BACs and sequential replacements can be either distal to proximal or proximal to distal.

Example 7

Engineering of Ig Loci Via Incorporation of Large BACs and Use of Site-Specific Recombinases in Embryonic Stem Cells Alternatively, sites for site-specific recombinases, such as loxP/CRE or frt/flp, can be employed to facilitate engineering of the Ig loci by introducing site-specific recombinase recognition sequences into DNAs to be introduced on the homologous recombination vectors, and then when the site-specific recombinase is expressed or introduced, recombination will occur between the sequences, therein deleting the intervening sequences. In this way two or more non-overlapping BACs are incorporated into the endogenous Ig locus via homologous recombination. The 5' BAC contains a loxP or frt recognition sequence in its 3' region while the 3' BAC contains a loxP or frt site in its 5' region, and the remaining endogenous sequence between the newly introduce sequences is removed via site-specific recombination.

Figure 4A:
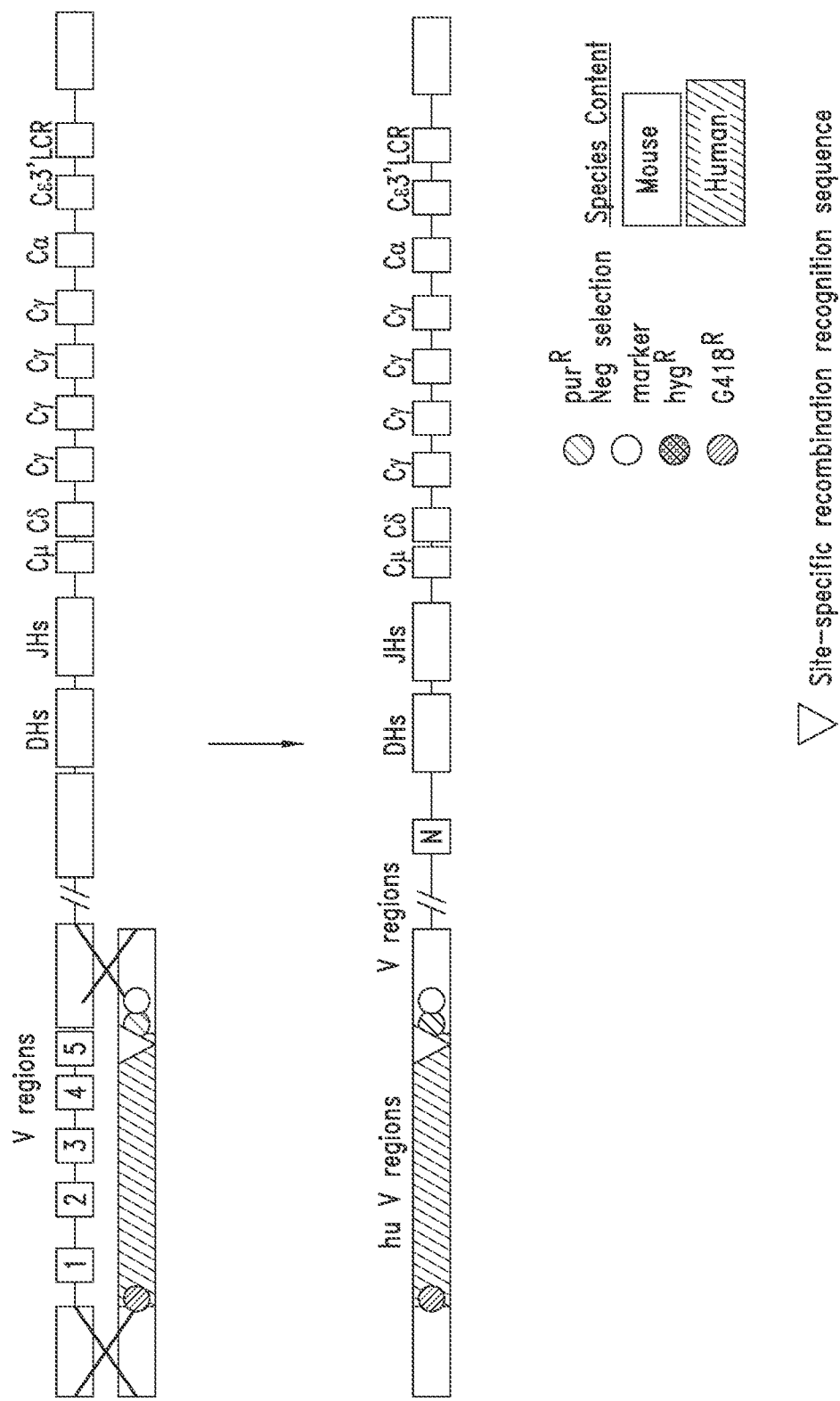
FIG. 4A is a diagram that depicts the introduction of a first BAC containing a recognition sequence for a site-specific recombinase into a mouse IgH locus via homologous recombination.
Figure 4B:
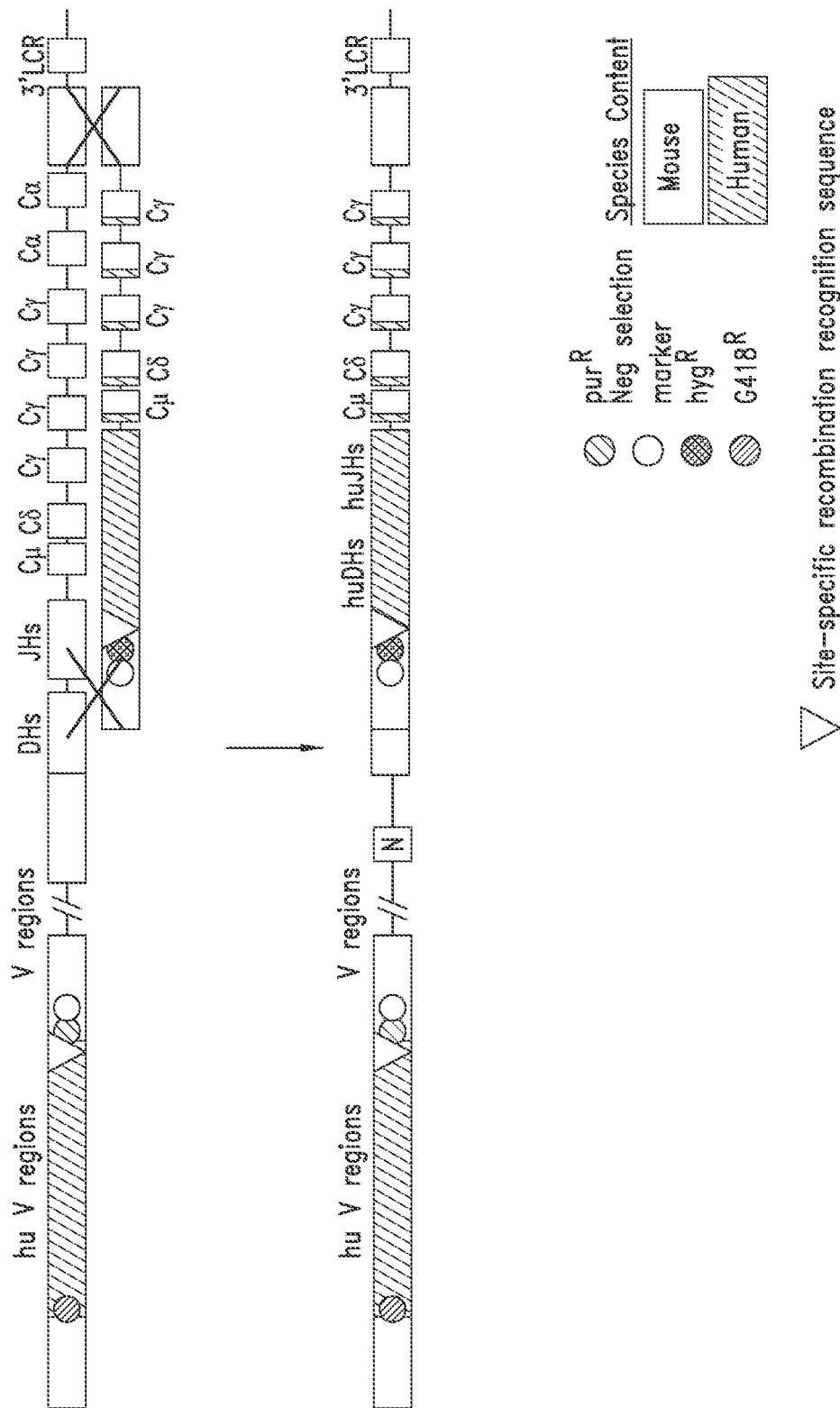
FIG. 4B is a diagram that shows the introduction of a second BAC containing a recognition sequence for a site-specific recombinase into the mouse IgH locus via homologous recombination.
Figure 4C:
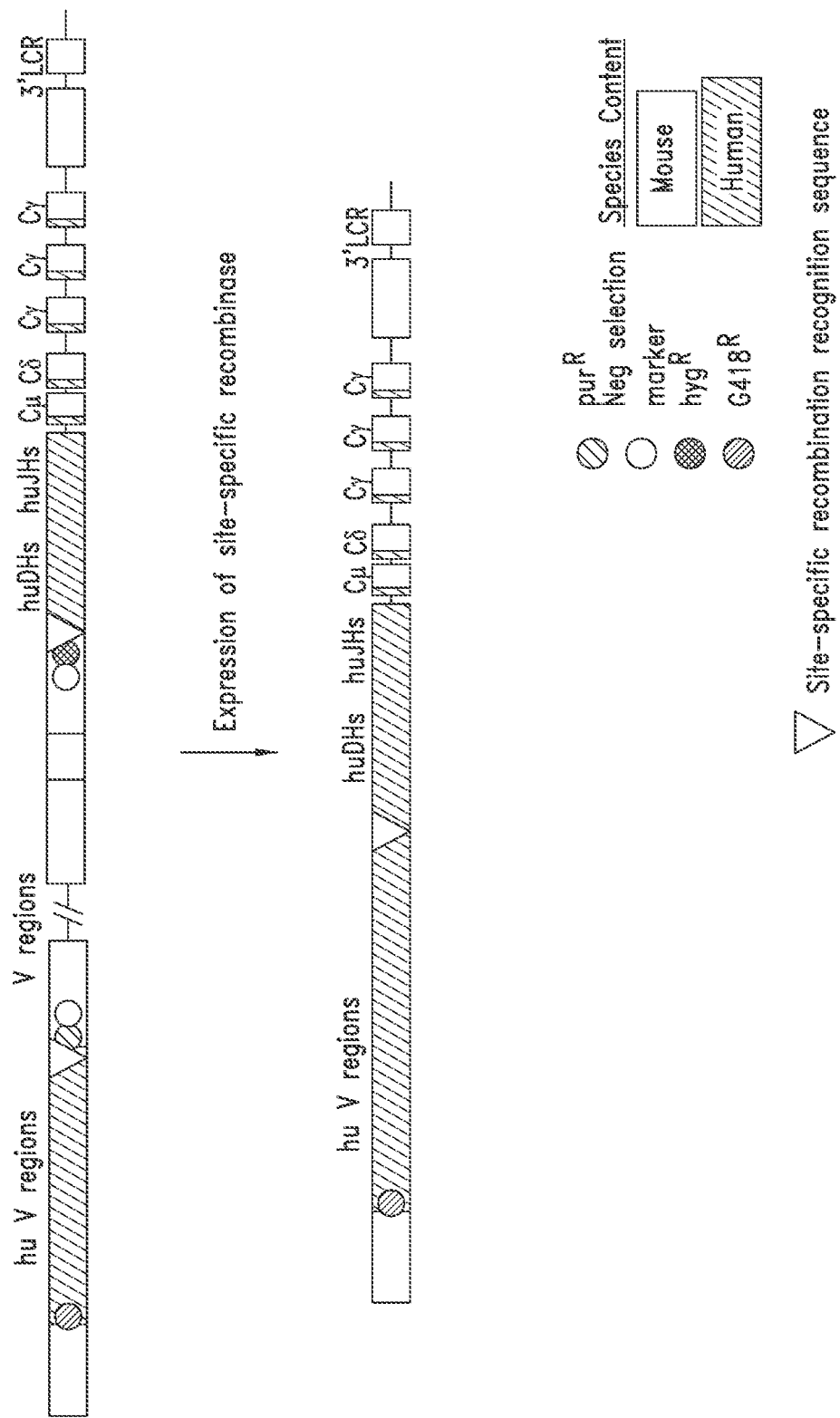
FIG. 4C is a diagram that illustrates the removal of the intervening sequences between the recognition sequences for a site-specific recombinase via introduction of the functional site-specific recombinase.
Figure 5A:
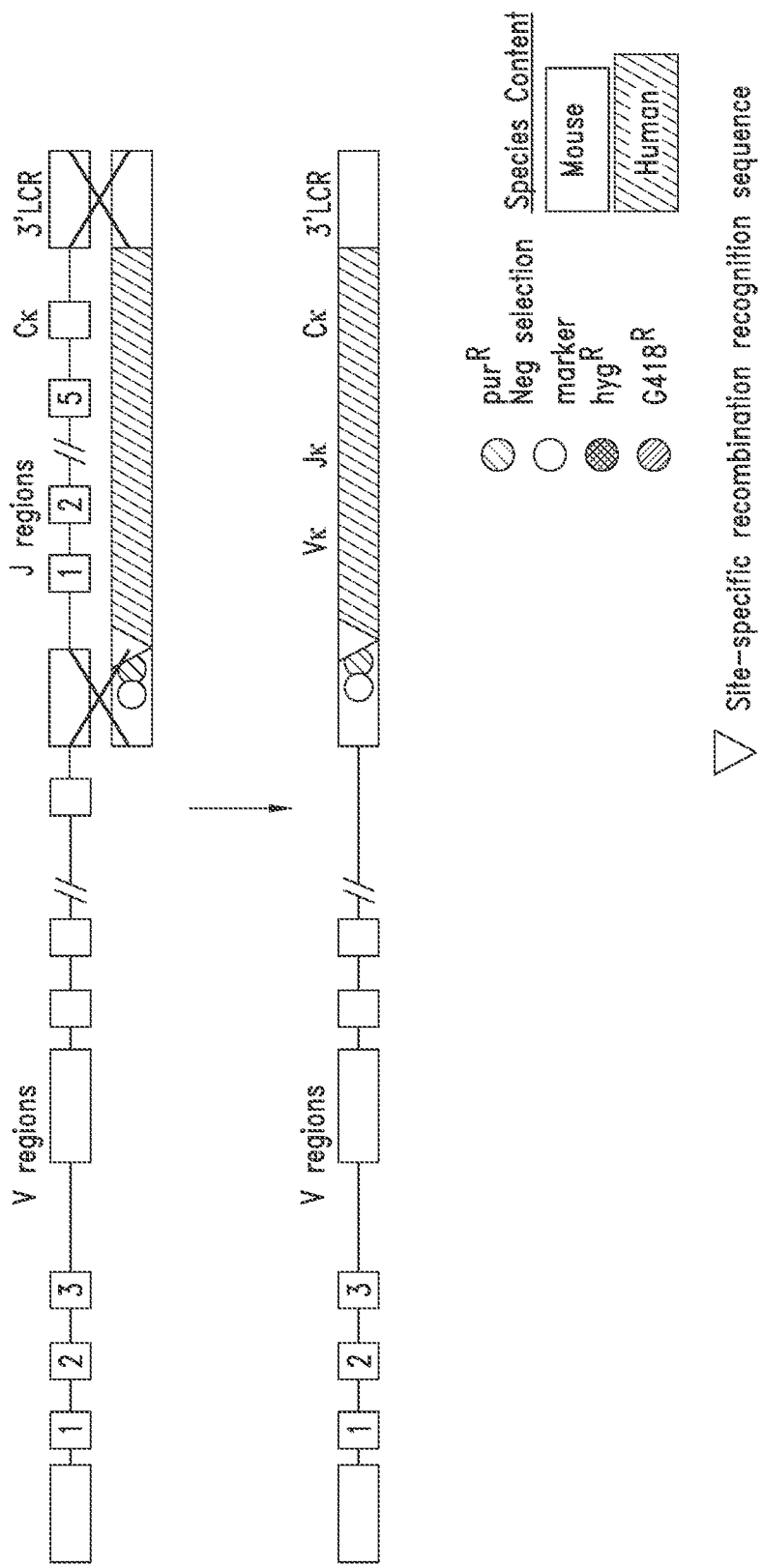
FIG. 5A is a diagram that depicts the introduction of a first BAC containing a recognition sequence for a site-specific recombinase into a mouse Igκ locus via homologous recombination.
Figure 5B:
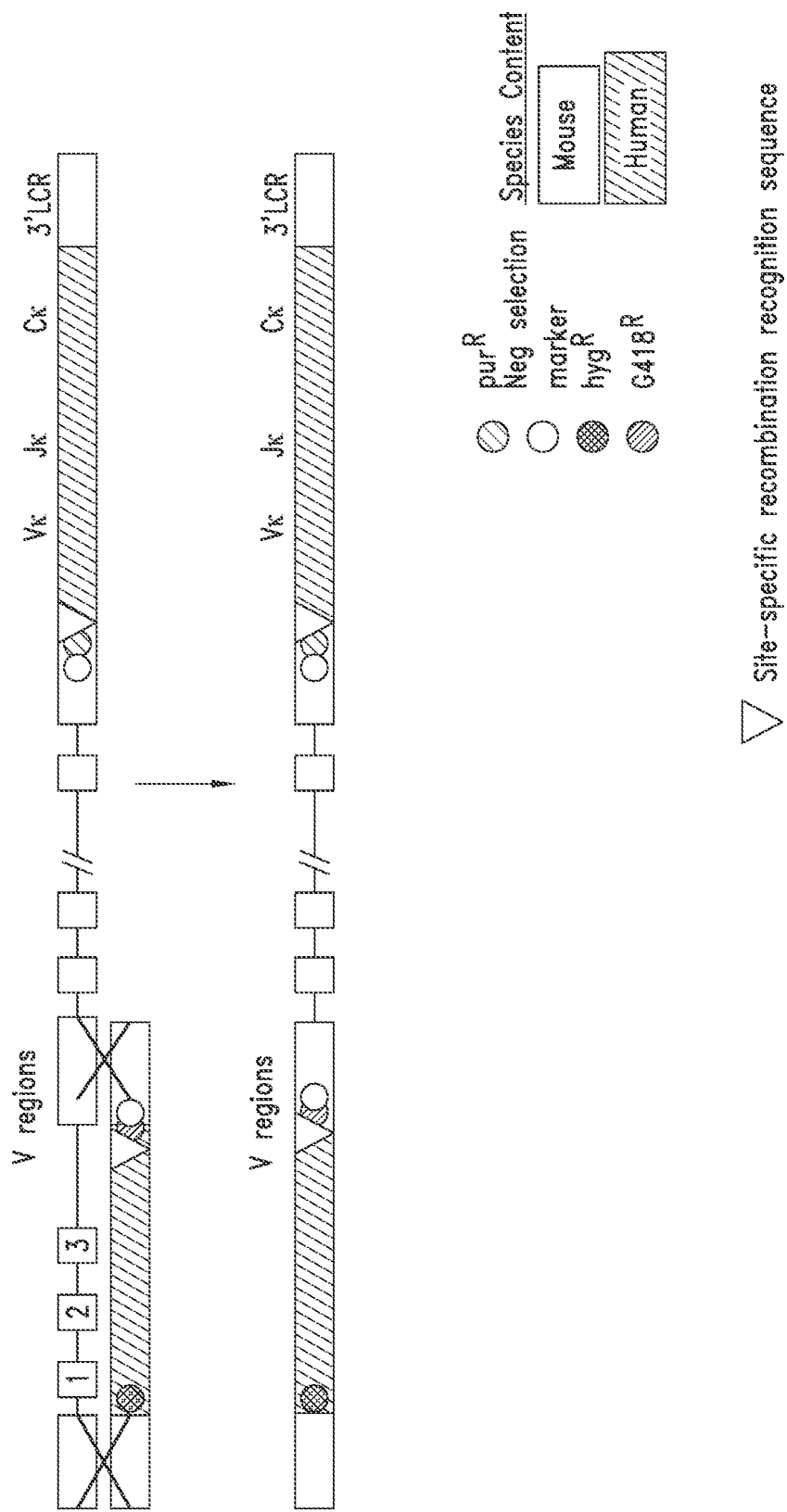
FIG. 5B is a diagram that shows the introduction of a second BAC containing a recognition sequence for a site-specific recombinase into the mouse Igκ locus via homologous recombination.
Figure 5C:
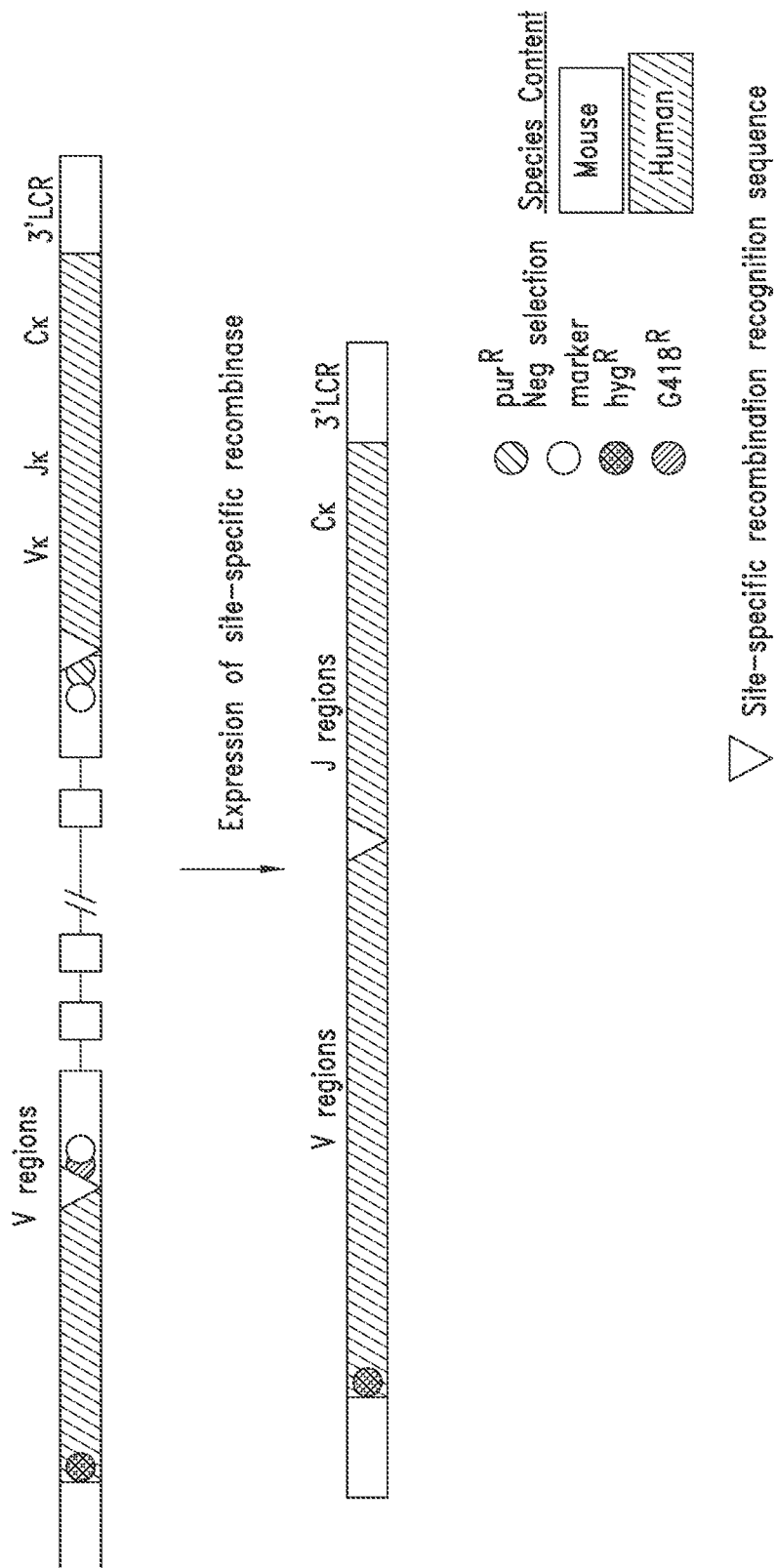
FIG. 5C is a diagram that illustrates the removal of the intervening sequences between the recognition sequences for a site-specific recombinase via introduction of the functional site-specific recombinase.

The BACs can be engineered to introduce loxP or frt sites that will flank the intervening sequences. Subsequently, expression of CRE or flp recombinase, respectively, in either the cells or the genetically engineered organism derived therefrom will trigger site-specific recombination between the loxP and frt sites, thereby deleting the intervening sequences (FIGS. 4 and 5).

After homologously recombined clones incorporating the second BAC targeting vector in the precise location have been identified, including performance of assay, e.g., fluorescent in situ hybridization with DNA probes from the first and second BAC, to confirm cis integration of the second BAC on the chromosome carrying the first BAC integrant, the first and second BACs are separated by an amount of intervening endogenous DNA from the mouse locus. The amount and content of this intervening endogenous DNA is determined by the location of the 3' flanking DNA on the first BAC and the 5' flanking DNA on the second BAC. This remaining intervening portion of the mouse sequence contained between the loxP ore frt sites that were introduced by homologous recombination is removed by CRE recombinase or flp recombinase. Either CRE recombinase or flp recombinase can be transiently expressed in clones that have both correctly targeted BAC inserts. CRE recombinase or flp recombinase acts efficiently and precisely upon loxP site or flp sites, respectively, therein deleting the intervening DNA between said sites. Confirmation of deletion and precise joining of the two BACs, 3' of the first BAC joined to the 5' of the second BAC, can be detected by Southern blots as described herein.

In yet another alternative, a lox P site and Cre recombinase can be used to selectively introduce a lox-site carrying exogenous DNA into a lox-P site already incorporated into the engineered Ig loci. In this way, additional DNA content can be introduced into the engineered loci.

Example 8

Sequential Replacement of Endogenous DNA from the 5' Direction

The direction of the replacement in homologous recombination-competent cells, such as ES cells, may be performed either from the 5' end or 3' end of the transcriptional direction. However, BAC modification should be done according to the configuration of the homology requirement for homologous recombination in competent cells.

For example, in the 5' end direction, the first BAC to be used has the telomere side of IgH V gene segments of the human sequence, flanked on either side by endogenous mouse DNA for targeting into the mouse IgH locus. The final BAC to be used in the iterative replacement process is a BAC modified as described above having human CH1 domains replacing mouse CH1 domains in some or all of the endogenous mouse C region constant regions. The DNA upstream of the mouse C region germline configured DNA (with the exception of CH1 domain replacement(s) and optionally upper and optionally also the middle hinge replacements) would be human DNA corresponding to a portion already integrated into the modified IgH locus and the downstream DNA would be mouse sequence 3' of the most 3' mouse Cγ on the replacing DNA to effect deletion of Cα and Cε and any Cγ gene segments but to leave unaffected the content of the mouse 3' LCR. As noted above, the flanking DNAs may range in size from 1 kb to 10 kb to 100 kb to larger.

Example 9

Sequential Replacement of Endogenous DNA from the 3' Direction

In the 3' direction, the first BAC is a modified BAC based on the last BAC for the 5' directional replacement. Furthermore, the first BAC has an additional 1 kb to 10 kb to 100 kb or greater mouse segment at the other side of the human sequence. For example, the 1 kb to 10 to 100 or greater kb segment starts from around the 5' end of the D region toward the telomere of the mouse chromosome. The last BAC is a modified BAC of the first BAC used for the replacement from 5' direction. The modification is an addition of 1 kb to 10 to 100 or greater kb of the mouse segment to the end of the human sequence. The 1 kb to 10 to 100 or greater kb region starts from the end of the first IgH V gene segment toward the outside of IgH.

Example 10

Homologous Recombination of the Igκ Locus

Figure 2A:
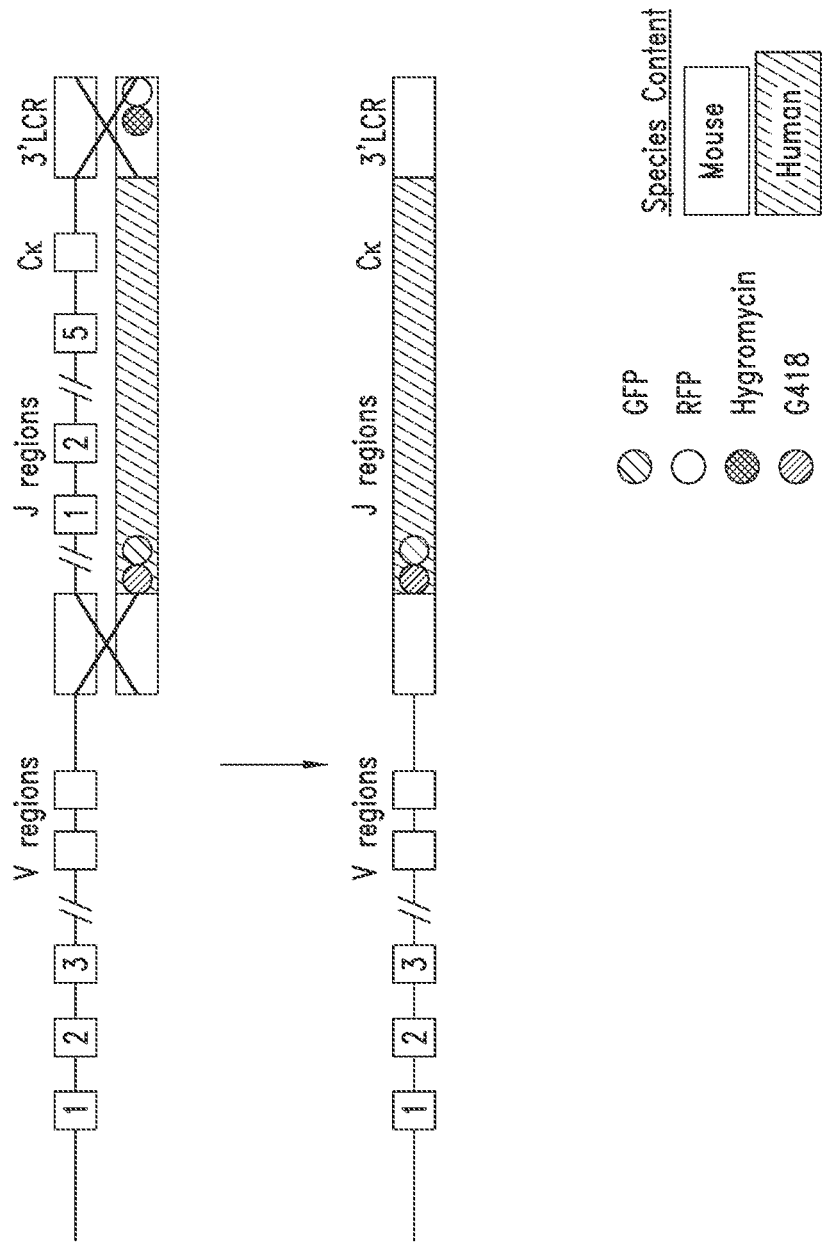
FIGS. 2A-2B depict the introduction of a human Igκ locus via sequential homologous recombination steps.
Figure 2B:
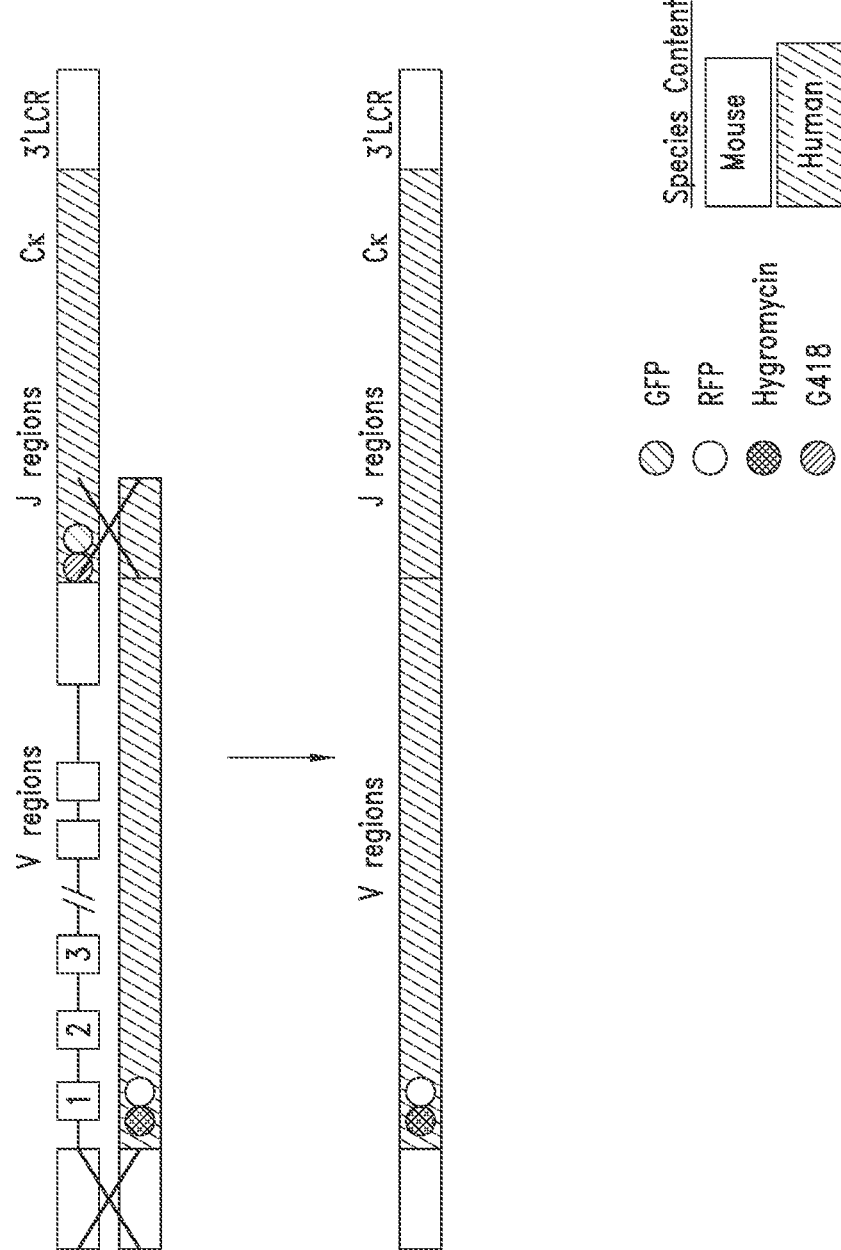

A replacement strategy as outlined above can also be performed on an Igκ locus endogenous in a cell chromosome, for example, in a mouse ES cell. To replace the endogenous mouse Vκ genes with the corresponding human Vκ gene content, only two iterative replacements may be required. This is because the human Vκ gene content is redundant, with the human Vκ genes being represented about 2 times, with a proximal cluster oriented in the same 5'-3' orientation as the Jκ and Cκ gene and this cluster duplicated in a distal, inverted orientation. This inverted, duplicated cluster represents only about 10% of the expressed Vκ repertoire in humans. Further, this distal, inverted duplication is missing from about 10% of humans. Consequently, as little as two overlapping BACs could comprise the unique human Vκ repertoire plus human Jκ genes and the human Cκ gene as shown in FIG. 2.

Alternatively, two non-overlapping BACs are homologously recombined into the Igκ locus, and each BAC introduces a site specific recombinase recognition sequence, such as loxP or frt. The 5' BAC contains, for example, a site-specific recombination recognition site in its 3' region, and the 3' BAC contains a site-specific recombination recognition site in its 5' region. Upon expression of the site-specific recombinase, the intervening mouse Igκ sequences between the two site-specific recombination recognition sites are deleted, thereby joining the sequences introduced by the BACs (FIG. 5).

Example 11

Homologous Recombination of the Igλ Locus

Figure 3A:
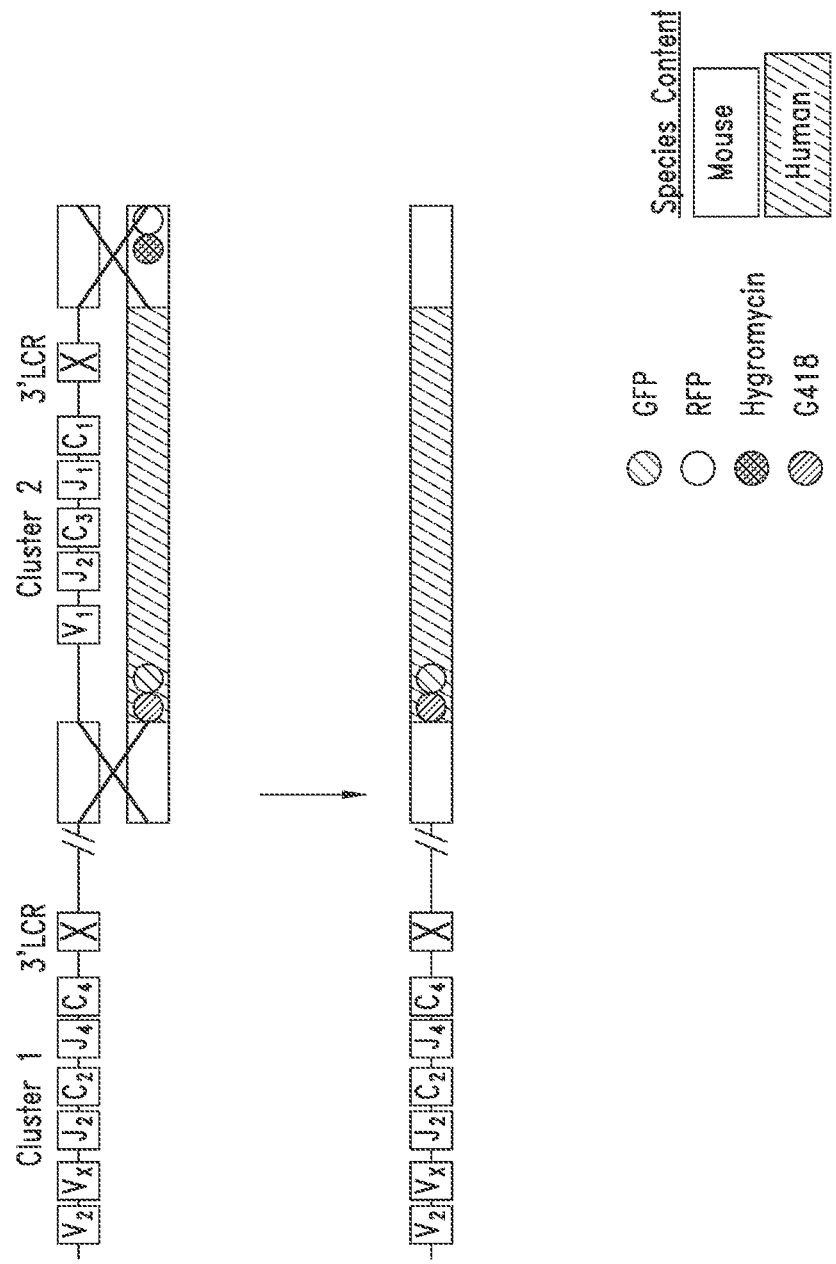
FIGS. 3A-3B depict the introduction of a human Igλ locus via sequential homologous recombination steps.
Figure 3B:
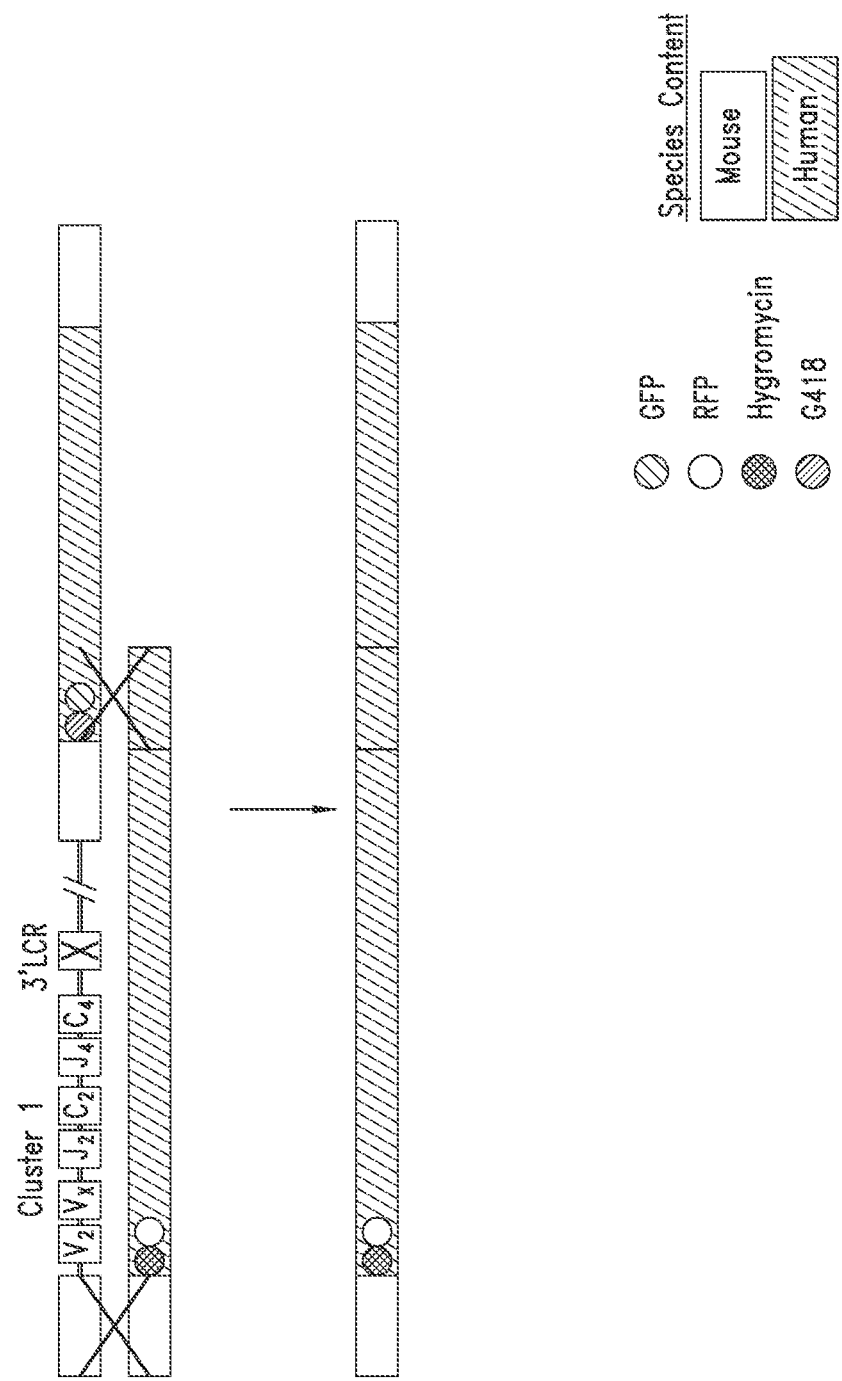

A replacement strategy as outlined above can also be performed on the Igλ locus endogenous in a cell chromosome, such as in a mouse ES cell. To replace the endogenous mouse Vλ genes with the corresponding human Vλ genes, only two iterative replacements may be required (FIG. 3). However, because the genomic organization of the Igλ locus is different in mouse versus humans, an alternative engineering strategy must be pursued to implant the human Igλ Vλ-Jλ genes. In mice, the Igλ locus consists of two separate but linked gene clusters, each composed of one or two Vλ genes upstream of two paired Jλ-Cλ gene sets. The most upstream Vλ only very rarely rearranges to the most downstream Jλ-Cλ pair. In humans, there are approximately 30 functional Vλ genes upstream of 7 Jλ-Cλ clusters.

Furthermore, leaving the mouse constant regions, specifically the mouse Igλ 3' LCRs, Eλ2-4 and/or Eλ3-1, intact and unmodified would likely lead to an engineered locus that would fail to express at the 60/40 κ:λ ratio of humans and rather would more likely express at the 95/5 κ:λ ratio of mice because of mutations, probably causing defects in NF-κB binding, that are present in the mouse Igλ 3' LCRs (see, e.g., Combriato and Klobeck, *J. Immunol.* 168:1259-

1266). Because the human Igλ locus contributes a substantial amount of diversity to the total human light chain repertoire it is beneficial to appropriately engineer the human Igλ BAC to recapitulate the genuine human immune response so as to increase the efficiency and probability of generating therapeutically useful mAbs against a broad range of antigen targets.

Engineered BACs replace the endogenous mouse Igλ locus with the human counterpart and restore a more fully functional Igλ 3' LCR downstream of the constant regions (FIG. 6). Several alternative strategies can be employed. The entire mouse Igλ locus can be replaced by the human locus by sequentially targeting a series of BACs that overlap across the human Igλ locus including the fully functional human Igλ 3' LCR into the mouse Igλ locus, sequentially replacing all of it, including the 3' LCRs. Alternatively, overlapping BACs can be engineered to contain all, or a portion of, the human Vλ genes and the 1-7 Jλ-Cλ pairs but with mouse Cλ genes replacing the human Cλ genes so that chimeric human Vλ-mouse Cλ Igλ chains are produced by the mouse. Alternatively, the human Igλ locus can be re-constructed on overlapping BACs to resemble the configuration of the human Igκ locus, with the complete set, or subset, of human Vλ genes, a cluster of 1-7 Jλ genes and a single selected human, or mouse, Cλ gene followed by the human 3' LCR. The inclusion of appropriate splice donor and splice acceptor sequences in the Jλ cluster and in the Cλ gene is confirmed, and if required, engineered into the BAC(s) in *E. coli* or during the chemical synthesis and assembly, prior to introduction into ES cells. This reconfigured locus rearranges and splices appropriately. However, it is possible that such a construct could rearrange more efficiently than in the germline configured human Igλ locus, therein leading to a proportionally higher representation of Igλ relative to Igκ in the light chain repertoire than is seen in humans.

Other configurations of the human locus and introductions into the mouse Igλ locus so as to produce human Igλ V regions conjoined with either human or mouse Cλ genes can be readily designed and engineered. Either the human Igλ 3'LCR region with functional NFκB binding sites or the mouse Igλ 3'LCR control with introduced mutations, e.g., by site-directed mutagenesis in vitro, to restore NFκB binding (see, e.g., Combriato and Klobeck, *J. Immunol.* 168:1259-1266), or a functional sub-portion of either one, such as DNAse I hypersensitive site 3 of the human Igλ 3'LCR, is included downstream of the final Cλ gene in a cluster in all constructs. Alternatively, a functional Igλ 3'LCR or functional sub-portion thereof from another species, e.g., rat, non-human primate, could be included. Alternatively, a functional Igκ 3' LCR from human, mouse or other species could be used.

Unless specifically deleted from or the sequence for which is not included in the chemically synthesized and assembled human DNA, the process of introducing the human Vλ repertoire will also introduce the genes for human surrogate light chain (SLC), which is within the human Vλ gene array in the germline DNA. Mouse SLC genes are linked to, but hundreds of kilobases separate from, the Igλ locus and would be unperturbed in this strategy so transgenic mice would co-express human and mouse SLC.

The human Vλ repertoire can be grouped into three clusters: A, B and C. The A cluster, most proximate to the J-C pairs, is the most frequently used, followed by the B and then the C cluster. One, two or three of these Vλ clusters may be incorporated. The strategy herein allows for engineering any or all or a portion thereof of the human Vλ clusters into the mouse genome, and replacing the endogenous mouse locus.

Example 12

Selection of Non-Human Mammalian Cells Following Homologous Recombination

To identify mammalian cells, such ES cells, that are the result of homologous recombination, a series of selection and screening procedures followed by molecular analyses are employed (FIGS. 1, 2 and 3). First, the cells are grown in the presence of a drug for which at least one drug-resistance gene is represented on the introduced BAC so as to select for cells that are stably carrying the BAC. The BAC may optionally carry a negative-selection marker such as thymidine kinase at the outside terminus of one or both of the flanking targeting regions to select against random integrants. Alternatively, clones positive for one drug resistance marker could be picked and duplicate plates made, one to test for drug resistance and one to test for drug sensitivity. Optionally, the BAC would also carry a screenable marker such as GFP or RFP approximately adjacent to the selectable marker. $GFP^+$ or $RFP^+$ clones could be detected by FACS or fluorescence microscopy. Both positive selectable and screenable markers are internal to the flanking targeting DNA so as to be stably integrated into the genome along with the replacing DNA.

To confirm homologous recombination on selected (drug resistant) and, optionally, screened (e.g., $GFP^+$) clones, genomic DNA is recovered from isolated clones and restriction fragment length polymorphism (RFLP) analysis performed by a technique such as Southern blotting with a DNA probe from the endogenous loci, said probe mapping outside the replaced region. RFLP analysis shows allelic differences between the two alleles, the endogenous DNA and incoming DNA, when the homologous recombination occurs via introduction of a novel restriction site in the replacing DNA. Because flanking DNA arms >10 kb in size may generate RFLPs that are large and difficult to resolve by standard agarose gel electrophoresis, low percentage agarose gels may be used or CHEF gel electrophoresis may be used. Flanking DNA arms of about 10 kb or less in size generate RFLPs that can be resolved by standard agarose gel electrophoresis. Alternatively, a restriction site may be purposely engineered into the replacing DNA on the BAC during replacement vector construction so as to engineer a conveniently sized fragment spanning the junction of the introduced DNA and the endogenous DNA upon restriction digest, and encompassing the designated probe sequence. In addition to RFLP analysis, cis integration may be screened using fluorescence in situ hybridization (FISH) to confirm the location of the introduced DNA according to methods known in the art.

Figure 6A:
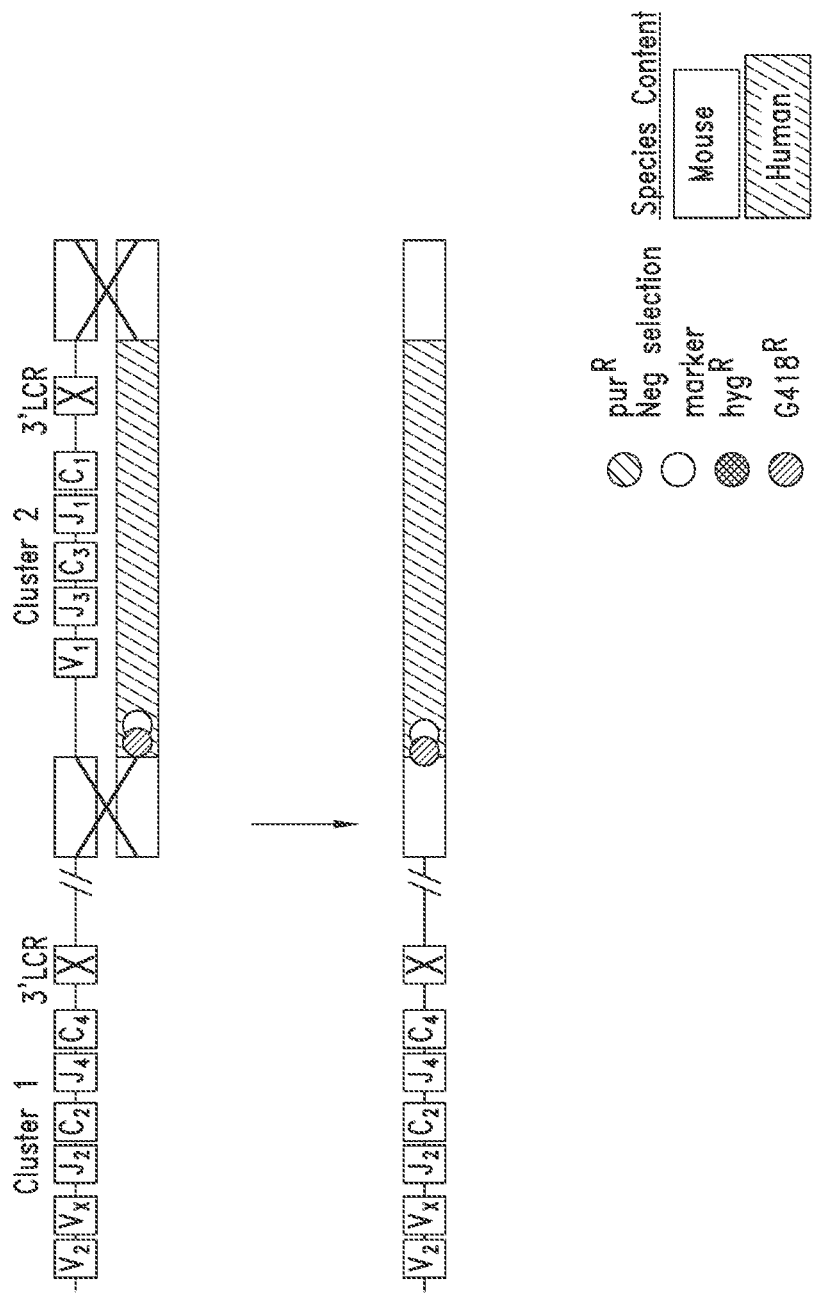
FIG. 6A is a diagram that depicts the introduction of a first BAC into a mouse Igλ locus via homologous recombination.

For subsequent engineering, different selectable and/or screenable markers are just internal to one flanking arm while the opposite flanking arm for homologous recombination, which overlaps with the flanking arm carrying the selectable and/or screenable markers used in targeting the BAC1, carries no markers, such that the homologous recombination event deletes the markers introduced in targeting BAC1 and introduces a new selectable and/or screenable marker at the opposite end (internal from the opposite flanking arm). For example, fluorescent markers alternate between GFP and RFP after each round of homologous recombination occurs such that round 1 introduces GFP and round 2 deletes GFP and introduces RFP. If random insertion occurs, both fluorescent markers exist in the ES cells. A flow cytometer with cell sorting capability can be utilized to sort and retain cells based on the presence of signals from one fluorescent protein and the absence of signal from another. Drug resistance markers can be used similarly, e.g., using a pair of positive and negative selection markers (FIGS. 6A and 6B).

Through standard advanced planning it should be possible to replace endogenous DNA with human DNA across megabase-sized loci through iterative rounds of homologous recombination using only 2 different pairs of combinations of one selectable marker and one screenable marker. However, three or more sets each of selectable and screenable markers could also be used.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for obtaining a human antibody, or an antigen-binding fragment thereof, that binds to a target antigen, which method comprises:
   a. immunizing a transgenic mouse with a target antigen, wherein the genome of the transgenic mouse comprises a first transgene comprising a chimeric immunoglobulin heavy chain (IgH) locus, or a portion thereof, the first transgene comprising in operable linkage from 5' to 3' an unrearranged DNA sequence of a human variable heavy chain (VH) gene segment, a human diversity heavy chain (DH) gene segment, and a human joining heavy chain (JH) gene segment, operably linked to a constant region gene comprising a human CH1 exon, a human C upper hinge exon, a mouse CH2 exon, and a mouse CH3 exon, wherein the human CH1 exon is selected from the group consisting of a human mu constant region (Cμ) CH1 exon, a human delta constant region (Cδ) CH1 exon, a human gamma-1 constant region (Cγ1) CH1 exon, a human gamma-2 constant region (Cγ2) CH1 exon, a human gamma-4 constant region (Cγ4) CH1 exon, a human alpha constant region (Cα) CH1 exon, and a human epsilon constant region (Cε) CH1 exon, wherein during B cell development, the IgH locus undergoes gene rearrangement and expresses the chimeric Ig heavy chain comprising a human heavy chain variable domain and a chimeric heavy IgH chain comprising the human CH1 domain, the human Cupper hinge region and the mouse CH2 and CH3 domains,
   wherein the genome further comprises a second transgene comprising a human Ig light chain (IgL) locus, or a portion thereof, wherein the IgL locus is unrearranged, wherein during B cell development, the IgL locus undergoes gene rearrangement and expresses a human Ig light chain comprising a human light chain variable domain functionally linked to a human light chain constant domain,
   b. allowing said transgenic mouse to mount an immune response to said antigen,
   c. isolating B lymphocytes from said transgenic mouse, wherein the isolated B lymphocytes comprise isolated B lymphocytes that produce an antigen-specific chimeric antibody that specifically binds to the target antigen, wherein the antigen-specific chimeric antibody comprises the chimeric Ig heavy chain and the human Ig light chain,
   d. creating individual monoclonal populations of said isolated B lymphocytes,
   e. screening said populations of B lymphocytes to identify a population that produces a monoclonal antibody directed to said antigen, wherein the monoclonal antibody comprises the chimeric Ig heavy chain and the human Ig light chain,
   f. isolating a polynucleotide comprising a sequence encoding the human heavy chain variable domain of the chimeric Ig heavy chain and a polynucleotide comprising a sequence encoding the human light chain variable domain of the human Ig light chain from the identified population of B lymphocytes, and
   g. expressing the polynucleotide comprising the sequence encoding the human heavy chain variable domain and the polynucleotide comprising the sequence encoding the human light chain variable domain.

2. The method according to claim 1, wherein the expressing step comprises implementing the polynucleotide comprising the sequence encoding the human heavy chain variable domain and the polynucleotide comprising the sequence encoding the human light chain variable domain into an in vitro antibody display system.

3. The method according to claim 1, further comprising appending the polynucleotide sequence encoding the human heavy chain variable domain to a sequence encoding a human heavy chain constant domain, thereby producing a DNA molecule encoding a fully human polypeptide comprising a human heavy chain variable domain and a human heavy chain constant domain.

4. The method according to claim 1, wherein the polynucleotide isolating step comprises single-cell PCR.

5. The method according to claim 4, wherein the single-cell PCR is single-cell RT-PCR.

6. The method according to claim 1, wherein the method further comprises generating hybridomas from the isolated B lymphocytes of step (c) before screening step (e).

7. The method of claim 1, further comprising appending the polynucleotide sequence encoding the human heavy chain variable domain to a sequence encoding a human heavy chain constant domain, and appending the polynucleotide sequence encoding the human light chain variable domain to a sequence encoding a human light chain constant domain, thereby producing a DNA molecule encoding a fully human antibody.

8. The method according to claim 7, wherein the expressing step comprises implementing the polynucleotide comprising the sequence encoding the human heavy chain variable domain and the polynucleotide comprising the sequence encoding the fully human VL-CL into an in vitro antibody display system.

9. The method according to claim 3, further comprising cloning the polynucleotide comprising the sequence encoding the fully human heavy chain variable domain and heavy chain constant domain into an expression vector, expressing an RNA and translating the RNA to produce a recombinant, fully human heavy chain variable domain-heavy chain constant domain polypeptide.

10. The method according to claim 7, further comprising cloning the polynucleotide encoding the human heavy chain variable domain and the heavy chain constant domain into an expression vector, cloning the polynucleotide encoding the human VL-CL polypeptide into an expression vector, expressing an RNA encoding the human heavy chain variable domain and the heavy chain constant domain and an RNA encoding the human VL-CL polypeptide and translating the RNAs to produce a recombinant fully human antibody.

11. The method according to claim 1, wherein the first transgene is randomly inserted.

12. The method according to claim 11, wherein all or a portion of the endogenous mouse Ig heavy chain locus is inactivated.

13. The method according to claim 1, wherein the first transgene is inserted by homologous recombination and replaces all or a portion of the endogenous mouse Ig heavy chain locus.

* * * * *